US007943174B2

(12) United States Patent
Oshlack et al.

(10) Patent No.: US 7,943,174 B2
(45) Date of Patent: May 17, 2011

(54) CONTROLLED RELEASE HYDROCODONE FORMULATIONS

(75) Inventors: Benjamin Oshlack, New York, NY (US); Hua-Pin Huang, Englewood Cliffs, NJ (US); John Masselink, Old Tappan, NJ (US); Alfred P. Tonelli, Congers, NY (US)

(73) Assignee: Purdue Pharma L.P., Stamford, CT (US)

( * ) Notice: Subject to any disclaimer, the term of this patent is extended or adjusted under 35 U.S.C. 154(b) by 0 days.

(21) Appl. No.: 10/864,829

(22) Filed: Jun. 9, 2004

(65) Prior Publication Data
US 2004/0266807 A1 Dec. 30, 2004

Related U.S. Application Data

(63) Continuation of application No. 09/702,283, filed on Oct. 30, 2000, now abandoned.

(60) Provisional application No. 60/162,541, filed on Oct. 29, 1999.

(51) Int. Cl.
*A61K 9/14* (2006.01)
*A21D 13/00* (2006.01)

(52) U.S. Cl. ........ 424/487; 424/464; 424/468; 424/469; 424/484; 424/486

(58) Field of Classification Search .................. 424/457, 424/458, 468–469, 473, 484, 485, 486–487, 424/488, 489, 490, 472, 464
See application file for complete search history.

(56) References Cited

U.S. PATENT DOCUMENTS

| | | | |
|---|---|---|---|
| 2,738,303 A | 3/1956 | Blythe | 167/82 |
| 3,634,584 A | 1/1972 | Poole | 424/21 |
| 3,845,770 A | 11/1974 | Theeuwes et al. | 128/260 |
| 3,870,790 A | 3/1975 | Lowey et al. | 424/19 |
| 3,916,889 A | 11/1975 | Russell | 128/145.8 |
| 3,916,899 A | 11/1975 | Theeuwes et al. | 128/260 |
| 4,063,064 A | 12/1977 | Saunders et al. | 219/121 |
| 4,088,864 A | 5/1978 | Theeuwes et al. | 219/121 LM |
| 4,132,753 A | 1/1979 | Blichare et al. | 264/75 |
| 4,377,568 A | 3/1983 | Chopra | 424/31 |
| 4,385,078 A | 5/1983 | Onda et al. | 427/3 |
| 4,389,393 A | 6/1983 | Schor et al. | 424/19 |
| 4,421,736 A | 12/1983 | Walters | 424/19 |
| 4,443,428 A | 4/1984 | Oshlack | 424/22 |
| 4,467,378 A | 8/1984 | Hussain | 424/260 |
| 4,483,847 A | 11/1984 | Augart | 424/22 |
| 4,520,172 A | 5/1985 | Lehmann et al. | 525/369 |
| 4,548,990 A | 10/1985 | Mueller et al. | 525/123 |
| 4,557,925 A | 12/1985 | Lindahl et al. | 424/19 |
| 4,600,645 A | 7/1986 | Ghebre-Sellassie et al. | 428/403 |
| 4,609,542 A | 9/1986 | Panoz et al. | 424/19 |
| 4,708,874 A | 11/1987 | De Haan et al. | 424/470 |
| 4,728,513 A | 3/1988 | Ventouras | 424/461 |
| 4,797,410 A | 1/1989 | El-Fakahany | 514/356 |
| 4,806,337 A | 2/1989 | Snipes et al. | 71/65 |
| 4,828,836 A | 5/1989 | Elger et al. | 424/419 |
| 4,834,984 A | 5/1989 | Goldie et al. | 424/488 |
| 4,834,985 A | 5/1989 | Elger et al. | 424/488 |
| 4,844,907 A | 7/1989 | Elger et al. | 424/465 |
| 4,844,909 A | 7/1989 | Goldie | 424/480 |
| 4,861,596 A | 8/1989 | Curtiss et al. | |
| 4,861,598 A | 8/1989 | Oshlack | 424/468 |
| 4,894,234 A | 1/1990 | Sharma et al. | 424/440 |
| 4,935,246 A | 6/1990 | Ahrens | 424/490 |
| 4,959,219 A | 9/1990 | Chow et al. | |
| 4,970,075 A | 11/1990 | Oshlack | 424/451 |
| 4,983,730 A | 1/1991 | Domeshek et al. | 536/69 |
| 4,990,341 A | 2/1991 | Goldie et al. | 424/484 |
| 4,996,047 A | 2/1991 | Kelleher et al. | |
| 5,007,790 A | 4/1991 | Shell | 424/451 |
| 5,019,397 A | 5/1991 | Wong et al. | 424/473 |
| 5,023,089 A | 6/1991 | Sakamoto et al. | 424/502 |
| 5,024,842 A | 6/1991 | Edgren et al. | 424/473 |
| 5,026,560 A | 6/1991 | Makino et al. | 424/494 |
| 5,030,400 A | 7/1991 | Danielsen et al. | 264/101 |
| 5,068,110 A | 11/1991 | Fawzi et al. | 424/461 |
| 5,071,646 A | 12/1991 | Malkowska et al. | 424/497 |
| 5,122,384 A | 6/1992 | Paradissis et al. | 424/451 |
| 5,126,145 A | 6/1992 | Evenstad et al. | 424/465 |
| 5,132,142 A | 7/1992 | Jones et al. | 427/196 |
| 5,133,974 A | 7/1992 | Paradissis et al. | 424/480 |
| 5,167,964 A | 12/1992 | Muhammad et al. | 424/482 |
| 5,169,645 A | 12/1992 | Shukla et al. | 424/499 |
| 5,178,868 A | 1/1993 | Malmqvist et al. | 424/490 |
| 5,196,203 A | 3/1993 | Boehm | 424/469 |
| 5,202,128 A * | 4/1993 | Morella et al. | 424/469 |
| 5,206,030 A | 4/1993 | Wheatley et al. | 424/490 |
| 5,219,575 A | 6/1993 | Von Bommel et al. | 424/490 |
| 5,248,516 A | 9/1993 | Wheatley et al. | 427/3 |
| 5,258,436 A | 11/1993 | Wheatley et al. | 524/388 |
| 5,266,331 A | 11/1993 | Oshlack et al. | 424/468 |

(Continued)

FOREIGN PATENT DOCUMENTS

AU 9047732 7/1990

(Continued)

OTHER PUBLICATIONS

Encarta World English Dictionary [North American Edition] 2006 Microsoft Incorporation "Matrix", p. 1, definition 2, http://encarta.msn.com/encnet/features/dictionary/DictionaryResults.aspx?refid=1861678516 retrieved on Apr. 30, 2006.*

(Continued)

*Primary Examiner* — T. D. Wessendorf
(74) *Attorney, Agent, or Firm* — Davidson, Davidson & Kappel LLC

(57) ABSTRACT

A solid oral controlled-release oral dosage form of hydrocodone is disclosed. The dosage form comprising an analgesically effective amount of hydrocodone or a pharmaceutically acceptable salt thereof, and a sufficient amount of a controlled release material to render the dosage form suitable for twice-a-day administration to a human patient, the dosage form providing a $C_{12}/C_{max}$ ratio of 0.55 to 0.85, said dosage form providing a therapeutic effect for at least about 12 hours.

29 Claims, 3 Drawing Sheets

U.S. PATENT DOCUMENTS

| | | | |
|---|---|---|---|
| 5,273,760 A | 12/1993 | Oshlack et al. | 424/480 |
| 5,283,065 A | 2/1994 | Doyon et al. | 424/467 |
| 5,286,493 A | 2/1994 | Oshlack et al. | 424/468 |
| 5,292,461 A | 3/1994 | Juch et al. | 264/37 |
| 5,321,012 A | 6/1994 | Mayer et al. | 514/25 |
| 5,330,766 A | 7/1994 | Morella et al. | 424/490 |
| 5,356,467 A | 10/1994 | Oshlack et al. | 106/161.1 |
| 5,378,474 A | 1/1995 | Morella et al. | 424/469 |
| 5,384,130 A | 1/1995 | Kamada | 424/461 |
| 5,411,745 A | 5/1995 | Oshlack et al. | 424/456 |
| 5,456,923 A | 10/1995 | Nakamichi et al. | 424/489 |
| 5,460,826 A | 10/1995 | Merrill et al. | 424/470 |
| 5,472,712 A | 12/1995 | Oshlack et al. | 424/480 |
| 5,478,577 A | 12/1995 | Sackler et al. | 424/489 |
| 5,500,227 A | 3/1996 | Oshlack et al. | 424/476 |
| 5,502,058 A | 3/1996 | Mayer et al. | 514/289 |
| 5,508,042 A | 4/1996 | Oshlack et al. | 424/468 |
| 5,518,730 A | 5/1996 | Fuisz | |
| 5,520,931 A | 5/1996 | Persson et al. | 424/473 |
| 5,549,912 A | 8/1996 | Oshlack et al. | 424/468 |
| 5,580,578 A | 12/1996 | Oshlack et al. | 424/468 |
| 5,593,695 A | 1/1997 | Merrill et al. | 424/480 |
| 5,601,842 A | 2/1997 | Bartholomaeus | 424/464 |
| 5,614,218 A | 3/1997 | Olsson | 424/456 |
| 5,629,011 A | 5/1997 | Illum | 424/434 |
| 5,637,320 A | 6/1997 | Bourke et al. | 424/489 |
| 5,639,476 A * | 6/1997 | Oshlack et al. | 424/468 |
| 5,656,295 A | 8/1997 | Oshlack et al. | 424/468 |
| 5,667,805 A | 9/1997 | Merrill et al. | 424/473 |
| 5,670,172 A | 9/1997 | Buxton et al. | 424/495 |
| 5,672,360 A | 9/1997 | Sackler et al. | 424/490 |
| 5,681,585 A | 10/1997 | Oshlack et al. | 424/494 |
| 5,843,480 A | 12/1998 | Miller et al. | 424/484 |
| 5,849,240 A | 12/1998 | Miller et al. | 264/460 |
| 5,866,161 A | 2/1999 | Childers et al. | |
| 5,879,705 A | 3/1999 | Heafield et al. | 424/464 |
| 5,891,471 A | 4/1999 | Miller et al. | 424/468 |
| 5,958,452 A | 9/1999 | Oshlack et al. | 424/457 |
| 5,958,459 A * | 9/1999 | Chasin et al. | 424/490 |
| 5,965,161 A | 10/1999 | Oshlack et al. | |
| 5,965,163 A | 10/1999 | Miller et al. | 424/468 |
| 5,968,551 A | 10/1999 | Oshlack et al. | 424/456 |
| 6,103,261 A | 8/2000 | Chasin et al. | 424/459 |
| 6,143,322 A | 11/2000 | Sackler et al. | 424/459 |
| 6,162,467 A * | 12/2000 | Miller et al. | 424/468 |
| 6,294,195 B1 | 9/2001 | Oshlack et al. | |
| 6,491,945 B1 * | 12/2002 | Childers et al. | 424/465 |
| 6,572,885 B2 | 6/2003 | Oshlack et al. | |
| 6,696,066 B2 * | 2/2004 | Kaiko et al. | 424/400 |
| 6,733,783 B2 | 5/2004 | Oshlack et al. | |

FOREIGN PATENT DOCUMENTS

| | | |
|---|---|---|
| AU | 9341654 | 2/1995 |
| AU | 1999 44493 | 10/1999 |
| CA | 2082573 | 11/1992 |
| CA | 2131350 A1 | 1/1994 |
| EP | 0097523 B1 | 6/1983 |
| EP | 0097523 A2 | 1/1984 |
| EP | 0108218 A2 | 5/1984 |
| EP | 0147780 A2 | 7/1985 |
| EP | 0235986 B1 | 2/1987 |
| EP | 0235986 B2 | 2/1987 |
| EP | 0253104 B1 | 5/1987 |
| EP | 0235986 A1 | 9/1987 |
| EP | 0253104 A1 | 1/1988 |
| EP | 0267702 A3 | 5/1988 |
| EP | 0271193 | 6/1988 |
| EP | 0271193 B1 | 6/1988 |
| EP | 0327295 | 8/1989 |
| EP | 0377518 A3 | 1/1990 |
| EP | 0388954 A3 | 3/1990 |
| EP | 0388954 B1 | 3/1990 |
| EP | 0361910 A1 | 4/1990 |
| EP | 0377517 A2 | 7/1990 |
| EP | 0377518 A2 | 7/1990 |
| EP | 0377518 B1 | 7/1990 |
| EP | 0388954 A2 | 9/1990 |
| EP | 0415693 A1 | 3/1991 |
| EP | 0452145 A2 | 10/1991 |
| EP | 0534628 B1 | 4/1992 |
| EP | 0532348 A3 | 9/1992 |
| EP | 0532348 B1 | 9/1992 |
| EP | 0532348 A2 | 3/1993 |
| EP | 0533297 A1 | 3/1993 |
| EP | 0534628 A1 | 3/1993 |
| EP | 0535841 A1 | 4/1993 |
| EP | 0546676 A1 | 6/1993 |
| EP | 0548448 A1 | 6/1993 |
| EP | 0553392 A1 | 8/1993 |
| EP | 0580860 A1 | 2/1994 |
| EP | 0636370 B1 | 6/1994 |
| EP | 0361680 B1 | 7/1994 |
| EP | 0609961 A1 | 8/1994 |
| EP | 0430287 B1 | 10/1994 |
| EP | 0636370 A1 | 2/1995 |
| EP | 0647448 A1 | 4/1995 |
| EP | 0665010 A1 | 8/1995 |
| EP | 1442745 | 8/2004 |
| GB | 2053681 B | 4/1984 |
| GB | 2170104 | 7/1986 |
| GB | 2178313 A | 2/1987 |
| JP | 40081086 | 4/1992 |
| WO | WO 9201446 | 2/1992 |
| WO | WO 9202209 A1 | 2/1992 |
| WO | WO 9206679 | 4/1992 |
| WO | WO 9208459 | 5/1992 |
| WO | WO 9304675 | 3/1993 |
| WO | WO 9307859 A1 | 4/1993 |
| WO | WO 9307861 | 4/1993 |
| WO | WO93/10765 | 6/1993 |
| WO | WO 93/10765 * | 6/1993 |
| WO | WO 9310765 | 6/1993 |
| WO | WO 9318753 | 9/1993 |
| WO | WO 9403160 | 2/1994 |
| WO | WO 9403161 | 2/1994 |
| WO | WO 9405262 | 3/1994 |
| WO | WO 9422431 | 10/1994 |
| WO | WO 95/14460 | 6/1995 |
| WO | WO 9600066 | 1/1996 |
| WO | WO 9601629 | 1/1996 |
| WO | 9608253 | 3/1996 |
| WO | WO96/08253 | 3/1996 |
| WO | WO 96/14058 | 5/1996 |
| WO | WO96/14058 | 5/1996 |
| WO | WO 9614058 | 5/1996 |
| WO | 9733566 A2 | 9/1997 |
| WO | WO 98/41194 | 9/1998 |
| WO | WO 01/32148 | 5/2001 |
| WO | WO 02/087512 | 7/2002 |

OTHER PUBLICATIONS

Wiktionary, "dispersed", p. 1, http://en.wiktionary.org/wiki/disperse retrieved on Apr. 30, 2006.*

Castensen et al., "USP Dissolution IV: Comparison of Methods" J. Pham. Sci. 1978, 67(9), pp. 1303-1307.*

Santus G., and Baker. R.W., "Osmotic drug delivery: a review of the patent literature", J Controlled Release (1995) vol. 35 pp. 1-21.

Hansch et al., "Comprehensive Medicinal Chemistry, vol. 5, Biopharmaceutics," Oxford, Pergamon Press, 1990, pp. 251-278.

Ratain et al., "Population pharmacodynamic study of amonafide: A cancer and leukemia group B study," Journal of Clinical Oncology, Grune and Stratton, 1995, pp. 741-747.

Database Medline Online! US National Library of Medicine, Yasuhara "Ethnic factors in evaluation of drug efficacy and safety".

Setiabudi et al., "Dapsone N-acetylation, Metoprolol, alpha-hydroxylation, and S-mephenytoin 4-hydroxylation polymorphisms in an Indonisian population: A cocktail and extended phenotyping assessment trial," Clinical Pharmacology & Therapeutics, 1994, pp. 141-153.

Database internet "Online!" Helsinki Declaration.

English translation of Office Action issued by Japanese Patent Office in connection with corresponding Japanese Patent Application No. 2001-534353 on May 25, 2010.

Merk Index, 13th edition, entry 4806: hydrocodone (2001).
EPI Journal Feb. 2007, pp. 59-60; David Harrison; "Divisional Application a continuing problem" (2007).
Document CA/PL 17/07; "Misuse of Divisional Applications," by the EPO Pressident, addressed to the EPO Committee of Patent Law. Presented at the EPO Administrative Council, dated Oct. 5, 2007.
Document CA/PL 3/08, presented by epi and other Professional Representatives, addressed to the EPO Committee of Patent Law. Presented at the EPO Administrative Council, dated Feb. 14, 2008.
Summons to Attend Oral Proceedings issued in connection with European Patent Application No. 05019453.9 on Jul. 23, 2010.
Abraham Sunshine, et al., "Analgesic oral efficacy of tramadol hydrochloride in postoperative pain," Clin. Pharmacol. Ther., Jun. 1992, pp. 740-746.
E. Beubler, "Medikamentose Schmerztherapie: Kriterien, Moglichkeiten, Risken," Therapiewoche Osterreich, 7, 2 (1992), pp. 1-15, English translation.
Geoffrey K. Gourlay, Ph.D., et al., "Influence of a high-fat meal on the absorption of morphine from oral solutions," Clin. Pharmacol. Ther., Oct. 1989, pp. 463-468.
Robert Kaiko, et al., "A Single-Dose Study of the Effect of Food Ingestion and Timing of Dose Administration on the Pharmacokinetic Profile of 30-MG Sustained-Release Morphine Sulfate Tablets," Current Therapeutic Research, vol. 47, No. 5, May 1990, pp. 869-878.
Geoffrey K. Gourlay, Ph.D., "The Reproducibility of Bioavailability of Oral Morphine from Solution Under Fed and Fasted Conditions," Journal of Pain and Sympton Management, vol. 6., No. 7, Oct. 1991, pp. 431-436.
Robert F. Kaiko, et al., "Controlled-Release Morphine Bioavailability (MS Contin Tablets) in the Presence and Absence of Food," The Hospice Journal, vol. 6(4) 1990, pp. 17-30.
N. Yokokawa, et al., "Relationship between plasma concentration of morphine and analgesic effectiveness," Postgrad Med J, (1991) 67 (Suppl. 2) pp. S50-S54.
Physicians Desk Reference 1994, 48th Edition, pp. 1821-1824.
D.L. Munday, "Changes in Drug Release Rate 2, Effect of Temperature and Relative Humidity on Polymeric Film Coatings," 5th Cong. Int. Tech. Pharm., 1989, vol. 2, pp. 55-60.
A Protocol for a clinical study entitled "A Randomized, Double-Blind, Parallel-Group Study comparing the Efficacy and Safety of Kapanol® to MsContin® in the Management of Patients with Moderate to Severe Cancer Pain" ("The Protocol"). The date of the Protocol is indicated as Feb. 10, 1992 and it bears COD No. 14556. The sponsor of the study is indicated to be Faulding Pharmaceuticals, an Australian company.
Certain Patient Diary Cards, Drug Disposition Records, Case Reports Forms and a listing which apparently correlates patient randomization number with the treatment of dosing regimen assigned to each patient.
Patient consent forms, apparently for four study participants.
Investigator Agreements between the study organizers and certain of the principal investigators.
Abstracts from the Twelfth Annual Congress of the Oncology Nursing Society, May 1987.
J. Lapin et al., "Cancer Pain Management with a Controlled Release Oral Morphine Preparation," Journ. Of Pain and Sympton Manag., v 4 (3), pp. 146-151, 1989.
J. Lapin et al., "Guidelines for use of Controlled Release Oral Morphine in Cancer pain Management," Cancer Nursing, v 12 (4), pp. 202-208, 1989.
R.F. Kaiko, "The Pre-and Postoperative Use of Controlled-Release Morphine (MS Contin Tablets): A Review of the Published Literature," Medical Department, The Purdue Frederick Company, Royal Society of Medical Services, International Congress, Symposium Services, No. 149, pp. 147-160 (1989).
H.F. Slowey et al., "Effect of Premedication with Controlled-Release Oral Morphine on Postoperative Pain," Anaesthesia, 1985, vol. 40, pp. 438-440.
MS Contin—Frequency of Daily Dosing, Jan.-Nov. 1990.
R.K. Portenoy, et al., "A Randomized, Double-Blind, Double-Dummy, Crossover Study Comparing the Pharmacokinetics and Pharmacodynamics of Kapanol® Capsules Given Every 24 hours and Every 12 hours with MS Contin® Tablets Given Every 12 Hours in the Management of Patients with Moderate to Severe Chronic Pain".
R. West et al., World Congress on Pain Abstracts 997-1001, Aug. 26, 1993.
Advertisement: Roxanol SR., 1988 Roxane Labs, Inc.
R. Kaiko and T. Hunt, Clip. Thera. vol. 13, No. 4, pp. 484-488, 1991.
S. Bloomfield, et al. Clin. Pharmacol. Ther. vol. 53, No. 4, pp. 469-478, 1993.
Advertisement: MS Contin 1986, 1987 The Purdue Frederick Company.
Sustained Release Medications, Noyes Data Corp., pp. 3,4, 10-15, 96-99, 335-337 (1980).
Flanders, P., et al., "The Control of Drug Release From Conventional Melt Granulation Matrices," Drug Development and Industrial Pharmacy, vol. 13, No. 6, pp. 1001-1022 (1987).
McTaggart, Celia M., et al., "The evaluation of formulation and processing conditions of a melt granulation process," International Journal of Pharmaceutics, vol. 19, pp. 139-148 (1984).
Schaefer, T., et al., "Melt granulation in a laboratory scale high shear mixer," Drug Development and Industrial Pharmacy, vol. 16, No. 8.\, pp. 1249-1277 (1990).
Thomsen, L. Juul, et al., "Prolonged Release Matrix Pellets Prepared by Melt Pelletization I. Process Variables," Drug Development and Industrial Pharmacy, vol. 19, No. 15, pp. 1867-1887 (1993).
Thomsen, L. Juul, et al., "Prolonged Release Matrix Pellets prepared by Melt Pelletization II. Hydrophobic Substances as Meltable Binders," Drug Development and Industrial Pharmacy, vol. 20, No. 77, pp. 1179-1197 (1994).
Thomsen, L.. Juul, "Utilizing melt pelletization technique for the preparation of prolonged release products," Pelletization, (material elaborated by assistant prof. Lars Juul Thomsen, Department of Pharmaceutics, Royal Danish School of Pharmacy for the DIE course "Pelletization Technologh," Nov. 1992, 106 pages plus 3 appendices.
Thomsen, L.. Juul, "Prolonged Release Matrix Pellets Prepared by Melt Pelletization. Part IV: Drug Particles Size, and Binder Composition," Pharmaceutical Technology Europa, pp. 19-24 (Oct. 1994).
Maccarrone C. et al.; Single Dose Pharmacokinetics of Kapanol™, a New Oral Sustained-Release Morphine Formulation; Clinical Drug Investigation 1994:7 (5) 262-274.
West R. J. Maccarrone C. Single dose pharmacokinetics of a new oral sustained release morphine formulation, Kapanol™ capsules. (Abstract 997) International Association for the Study of Pain, 7th World Congress on Pain. Paris, Aug. 22-27, 1993 (Data on file, Glaxo Australia, F.H. Faulding).
Gourlay GK, Plummer JL, Cherry DA, et al. A comparison of Kapanol™ (A new sustained release morphine formulation), MST Continus® and morphine solution in cancer patients: pharmacokinetic aspects. (Abstract 998) International Association for the Study of Pain, 7th World Congress on Pain. Paris, Aug. 22-27, 1993 (Data on file, Glaxo Australia, F.H. Faulding).
Cherry DA, Gourley GK, Plummer JL, et al. A comparison of Kapanol™ (a new sustained release morphine formulation), MST Continus® and morphine solution in cancer patients: morphine metabolite profiles and renal function. (Abstract 999) International Association for the Study of Pain, 7th World Congress on Pain, Paris, Aug. 22-27, 1993 (Data on file, Glaxo Australia, F.H. Faulding).
Plummer JL, Cherry DA, Gourlay GK, et al. A comparison of Kapanol™ (a new sustained release morphine formulation) MST Continus® and morphine solution in cancer patients: pharmacodynamic aspects. (Abstract 1000) International Association for the Study of Pain, 7th World Congress on Pain, Paris, Aug. 22-27, 1993 (Data on file, Glaxo Australia, F.H. Faulding).
Toner G, Cramond T, Bishop, et al. Randomized double blind, phase III crossover study of a new sustained-release oral morphine formulation, Kapanol™ capsules, (Abstract 1001) International Association for the Study of Pain, 7th World Congress on Pain, Paris, Aug. 22-27, 1993 (Data on file, Glaxo Australia, F.H. Faulding).
European Journal of Cancer; Once a Day (i.e. 24 Hourly) Kapanol™, A New Sustained Release Morphine Formulation, in the Treatment of Cancer Pain: Morphine Metabolite Profiles; Part A General Topics 1995; 31 (S5) Suppl:S184 Abs 884, European Conference on Clinical Oncology and Cancer Nursing, Paris, Oct. 29-Nov. 2, 1995.

European Journal of Cancer; Once A Day (i.e. 24 Hourly) Kapanol™, A New Sustained Release Morphine Formulation, In The Treatment of Cancer Pain: Pharmacokinetic Aspects; Part A General Topics 1995:31 (S5) Suppl: S187 Abs 897 European Conference on Clinical Oncology and Cancer Nursing, Paris, Oct. 29-Nov. 2, 1995.

European Journal of Cancer; Kadian™/Kapanol™—A Once Daily Morphine Formulation; Part A General Topics 1995;31 (S5) Suppl: S182 Abs 873 European Conference on Clinical Oncology and Cancer Nursing, Paris, Oct. 29-Nov. 2, 1995.

Gourlay et al., Proceeding of the 7$^{th}$ World Congress on Pain; A comparison of Kapanol (a New Sustained-Release Morphine Formulation), MST Continus, and Morphine Solution in Cancer Patients: Pharmacokinetic Aspects of Morphine and Morphine Metabolites Progress in Pain Research and Management vol. 2 pp. 631-643.

Kaiko R.F.; Clinical Protocol and Role of Controlled Release Morphine in the Surgical Patient; Anesthesiology and Pain Management 1991 pp. 193-212.

MS Contin—Frequency of Daily Dosing (NDTI)—Jun. 1991-May 1992.

The Merck Index, eleventh edition, pp. 757 and 1100 (1989).

* cited by examiner

CONTROLLED RELEASE HYDROCODONE FORMULATIONS

This application claims priority from U.S. Provisional Application Ser. No. 60/162,541 filed Oct. 29, 1999 which is hereby incorporated by reference.

BACKGROUND OF THE INVENTION

Due to the difficulties presented by the pharmacotherapy of pain, particularly chronic pain, opioid analgesics are ideal drugs to be administered as controlled release formulations. The present invention relates to a solid, controlled-release oral dosage form for use in the treatment of pain.

It is the intent of all controlled (slow) release formulations to provide a longer period of pharmacological action after administration than is ordinarily obtained after administration of immediate-release dosage forms. Such longer periods of response provide for many therapeutic benefits that are not achieved with corresponding short acting, immediate release preparations. Thus, therapy may be continued without interrupting the sleep of the patient, which is of special importance, for example, when treating a patient for moderate to severe pain (e.g., a post-surgery patient, a cancer patient, etc.), or for those patients who experience migraine headaches on awakening, as well as for the debilitated patient for whom sleep is essential.

Unless conventional rapid acting drug therapy is carefully administered at frequent intervals to maintain effective steady state plasma concentrations of the drug, peaks and valleys in the plasma level of the active drug occurs because of the rapid absorption, systemic excretion of the compound and through metabolic inactivation, thereby producing special problems in maintenance therapy of the patient. A further general advantage of longer acting drug preparations is improved patient compliance resulting from the avoidance of missed doses through patient forgetfulness.

It is known in the pharmaceutical art to prepare compositions which provide for controlled release of pharmacologically active substances contained in the compositions after oral administration to humans and animals. Such slow release compositions are used to delay absorption of a medicament until it has reached certain portions of the alimentary tract. Such controlled release of a medicament in the alimentary tract further maintains a desired concentration of said medicament in the blood stream for a longer duration than would occur if conventional rapid release dosage forms are administered.

The prior art teaching of the preparation and use of compositions providing the controlled release of an active compound from a carrier is basically concerned with the release of the active substance into the physiologic fluid of the alimentary tract. However, it is generally recognized that the mere presence of an active substance in the gastrointestinal fluids does not, by itself, ensure bioavailability.

In order to be absorbed, the active drug substance must be in solution. The time required for a given proportion of an active substance from a unit dosage form is determined as the proportion of the amount of active drug substance released from a unit dosage form over a specified time base by a test method conducted under standardized conditions. The physiologic fluids of the gastrointestinal tract are the media for determining dissolution time. The present state of the art recognizes many satisfactory test procedures to measure dissolution time for pharmaceutical compositions, and these test procedures are described in official compendia worldwide.

Although there are many diverse factors which influence the dissolution of a drug substance from its carrier, the dissolution time determined for a pharmacologically active substance from the specific composition is relatively constant and reproducible. Among the different factors which may affect the dissolution time are the surface area of the drug substance presented to the dissolution solvent medium, the pH of the solution, the solubility of the substance in the specific solvent medium, and the driving forces of the saturation concentration of dissolved materials in the solvent medium. Thus, the dissolution concentration of an active drug substance is dynamically modified in its steady state as components are removed from the dissolution medium through absorption across the tissue site. Under physiologic conditions, the saturation level of the dissolved materials is replenished from the dosage form reserve to maintain a relatively uniform and constant dissolution concentration in the solvent medium providing for a steady state absorption.

The transport across a tissue absorption site of the gastrointestinal tract is influenced by the Donnan osmotic equilibrium forces on both sides of the membrane since the direction of the driving force is the difference between the concentrations of active substance on either side of the membrane, i.e., the amount dissolved in the gastrointestinal fluids and the amount present in the blood. Since the blood concentrations are constantly being modified by dilution, circulatory changes, tissue storage, metabolic conversion and systemic excretion, the flow of active materials is directed from the gastrointestinal tract into the blood stream.

Various techniques have been used to prepare controlled release dosage forms. Specially coated pellets, tablets and capsules wherein the slow release of the active medicament is brought about through selective breakdown of the coating of the preparation or through compounding with a special matrix to affect the release of a drug are known in the art. Certain controlled release formulations provide for related sequential release of a single dose of an active compound at predetermined periods after administration.

Specific examples of controlled release opioid formulations reported in the patent literature include, for example, those disclosed in U.S. Pat. Nos. 4,990,341 and 4,844,909 (Goldie, et al.), both assigned to the assignee of the present invention and incorporated herein by reference, describe hydromorphone compositions wherein the dissolution rate in-vitro of the dosage form, when measured by the USP Paddle or Basket Method at 100 rpm in 900 ml aqueous buffer (pH between 1.6 and 7.2) at 37° C., is between 12.5 and 42.5% (by wt) hydromorphone released after 1 hour, between 25 and 55% (by wt) released after 2 hours, between 45 and 75% (by wt) released after 4 hours and between 55 and 85% (by wt) released after 6 hours, the in-vitro release rate being independent of pH between pH 1.6 and 7.2 and chosen such that the peak plasma concentration of hydromorphone obtained in-vivo occurs between 2 and 4 hours after administration of the dosage form. At least 12 hours of pain relief is obtained with these hydromorphone formulations.

It is considered highly desirable to provide controlled-release dosage formulations of other opioid analgesic drugs which can be used for moderate pain. It is further considered highly desirable to provide such controlled-release formulations with pharmacokinetic properties which provide the most effective pain management in patients in need of pain therapy.

SUMMARY OF THE INVENTION

It is an object of the present invention to substantially improve the efficiency and quality of pain management in human patients experiencing moderate pain.

It is an object of the present invention to provide bioavailable hydrocodone formulations that substantially improve the efficiency and quality of pain management.

It is yet another object of the present invention to provide bioavailable controlled-release hydrocodone formulations which provide a substantially increased duration of effect as compared to immediate release hydrocodone formulations, but which provide an early onset of analgesia.

It is a further object of the invention to provide orally administrable controlled release opioid formulations suitable for twice-a-day administration which provide an early onset of therapeutic effect and which, after rising to a maximum concentration during the dosage interval, provide a relatively flat serum plasma profile, meaning that the plasma level of the opioid provides a $C_{12}/C_{max}$ ratio of 0.55 to 0.85, and which provides effective pain relief to the patient. In alternate embodiments, the dosage form provides a $C_{12}/C_{max}$ ratio of 0.65 to 0.75 The above objects and others are attained by virtue of the present invention, which in certain embodiments, provides a solid oral controlled-release dosage form comprising an analgesically effective amount of hydrocodone or a pharmaceutically acceptable salt thereof and a sufficient amount of a controlled release material to render the dosage form suitable for twice-a-day administration, the dosage form after single administration to a human patient or a population of patients, providing a time to peak plasma concentration of hydrocodone in-vivo, preferably at from about 2 to about 8 hours (Tmax), and after attaining a maximum concentration, providing a $C_{12}/C_{max}$ ratio of 0.55 to 0.85.

In certain preferred embodiments, the controlled release dosage form provides an in-vitro release of from 18% to about 42.5% by weight of the hydrocodone or salt thereof from the dosage form at one hour when measured by the USP Basket Method at 100 rpm in 700 ml of Simulated Gastric Fluid (SGF) for 55 minutes at 37° C. and thereafter switching to 900 ml of Simulated Intestinal Fluid (SIF) at 37° C.

In certain preferred embodiments, the dissolution rate in-vitro of the hydrocodone dosage form when measured by the USP Basket method at 100 rpm in 900 ml aqueous buffer at a pH of 1.2 and 7.5 at 37° C. is from about 25 to about 65% by weight of the hydrocodone or salt thereof released after 2 hours, from about 45 to about 85% by weight of the hydrocodone or salt thereof released after 4 hours, and greater than about 60% by weight of the hydrocodone or salt thereof released after 8 hours. Although the in-vitro release rate may be either pH-independent or pH-dependent as desired, in preferred embodiments of the invention the release of hydrocodone is pH-independent.

In certain preferred embodiments, there is provided a controlled release dosage form comprising a therapeutically effective amount of hydrocodone wherein the dosage form provides a hydrocodone plasma plasma concentration of at least 5 or 6 ng/ml, at 12 hours after administration and provides a plasma plasma concentration of at least about 8 ng/ml at from about 2 to about 8 hours after administration.

In other preferred embodiments of the invention, there is provided a twice-a-day oral controlled release dosage form of hydrocodone which provides a Cmax of hydrocodone which is less than about 50% of the Cmax of an equivalent dose of an immediate release hydrocodone reference formulation (e.g. Lortab®), and which provides effective analgesia during the 12 hour dosage interval.

In other preferred embodiments of the invention, there is provided a twice-a-day controlled release dosage form of hydrocodone wherein the dosage form provides a time to 80% Cmax which is from about 90% to about 150%, preferably from about 90% to about 110%, of the time to 80% Cmax of an equivalent dose of immediate release hydrocodone reference formulation (e.g. Lortab). Preferably, the time to 80% Cmax of hydrocodone for the controlled release dosage form being from about 0.5 to about 1.5 hours, most preferably from about 0.8 to about 1.2 hours. In alternate embodiments, the time to 80% Cmax of hydrocodone for the controlled release dosage form is from about 0.75 to about 2.0 hours, most preferably from about 0.9 to about 1.5 hours.

In other preferred embodiments of the invention, there is provided a twice-a-day controlled release dosage form of hydrocodone wherein the dosage form provides a time to 90% Cmax which is about 150% to about 400%, preferably from about 150% to about 250%, of the time to 90% Cmax of an equivalent dose of immediate release hydrocodone reference formulation. Preferably, the time to 90% Cmax of hydrocodone for the controlled release dosage form is from about 1.5 to about 2.5 hours, most preferably from about 1.8 to about 2.2 hours. In alternate embodiments, the time to 90% Cmax of hydrocodone for the controlled release dosage form is from about 1.5 to about 4.0 hours, most preferably from about 1.8 to about 2.5 hours.

In other preferred embodiments of the invention, there is provided a twice-a-day controlled release dosage form of hydrocodone wherein the dosage form maintains a plasma concentration within 80% of Cmax from about 0.5 to 10 hours, preferably from about 1 to about 9 hours or from about 4 to about 8 hours.

In other preferred embodiments of the invention, there is provided a twice-a-day controlled release dosage form of hydrocodone which maintains a plasma plasma concentration of hydrocodone within 90% of Cmax from about 1 to 6.5 hours, preferably from about 2 to about 5 hours or from about 2 to about 6.5 hours.

In other preferred embodiments of the invention, there is provided a twice-a-day controlled release dosage form of hydrocodone which provides a mean in-vivo absorption rate from administration to Tmax from about 1.5 mg/hour to about 5 mg/hour and provides a mean rate of absorption from Tmax to the end of the dosing interval which is less than about 0.5 mg/hour based on oral administration of a dosage form containing 15 mg hydrocodone bitartrate. Preferably, the dosage form provides a mean in-vivo absorption rate from administration to Tmax from about 2 mg/hour to about 4 mg/hour and provides a mean in-vivo absorption rate Tmax to the end of the 12 hour dosing interval which is from about 0.08 mg/hour to about 0.4 mg/hour based on oral administration of a dosage form containing 15 mg hydrocodone bitartrate.

In other preferred embodiments of the invention, there is provided a twice-a-day oral controlled release hydrocodone dosage form which provides a rate of absorption during the time period from Tmax to about 12 hours after oral administration of the dosage form which is from about 55% to about 85% of the rate of elimination during the same time period.

The above embodiments of the invention, as well as other embodiments, preferably provide a time to Tmax at a time point 3 to 4 times later than the Tmax provided by an equivalent dose of an immediate release hydrocodone reference. Preferably, the Tmax provided by the sustained release formulation occurs at from about 2 to about 8 hours, from about 3 to about 7 hours or from about 4 to about 6 hours after oral administration.

The present invention is further directed to hydrocodone formulations which provide a Cmax of hydrocodone which is less than about 50%, preferably less than about 40% of the Cmax provided by an equivalent dose of an immediate release reference product.

For example, it was surprisingly discovered that when hydrocodone is formulated in the delivery system as disclosed in U.S. Pat. Nos. 4,861,598 and 4,970,075, the Cmax of hydrocodone provided by the delivery system as a percentage of the Cmax of an immediate release reference product was considerably lower than the same calculation for oxycodone formulated in the same delivery system. This phenomena is evident, regardless of the fact that the controlled release oxycodone and hydrocodone formulations exhibited similar in-vitro dissolution parameters.

When the present invention is formulated using the delivery systems U.S. Pat. Nos. 4,861,598 and 4,970,075, the Cmax of the delivery system as a percentage of the Cmax of the immediate release reference product is less than about 50%, and less than 40% in preferred embodiments, whereas oxycodone, exhibits a calculation of greater than 50%.

"Hydrocodone" is defined for purposes of the invention as including hydrocodone free base, as well as pharmaceutically acceptable salts and complexes of hydrocodone.

The term "USP Paddle or Basket Method" is the Paddle and Basket Method described, e.g., in U.S. Pharmacopoeia XXI (1990), herein incorporated by reference.

The term "pH-dependent" for purposes of the present invention is defined as having characteristics (e.g. dissolution) which vary according to environmental pH.

The term "pH-independent" for purposes of the present invention is defined as having characteristics (e.g., dissolution) which are substantially unaffected by pH.

The term "bioavailability" is defined for purposes of the present invention as the extent to which the drug (e.g., hydrocodone) is absorbed from the unit dosage forms.

The term "controlled-release" is defined for purposes of the present invention as the release of the drug (e.g., hydrocodone) at such a rate that blood (e.g., plasma) concentrations are maintained within the therapeutic range but below toxic concentrations over a period of time of about 12 hours or longer.

The term "Cmax" denotes the maximum plasma concentration obtained during the dosing interval.

The term "Tmax" denotes the time to maximum plasma concentration (Cmax).

The term $T_{1/2}$ (abs) denotes the amount of time necessary for one-half of the absorbable dose of opioid to be transferred to plasma.

The term "steady state" means that a plasma concentration for a given drug has been achieved and which is maintained with subsequent doses of the drug at a concentration which is at or above the minimum effective therapeutic concentration and is below the minimum toxic plasma concentration for a given drug. For opioid analgesics, the minimum effective therapeutic concentration will be a partially determined by the amount of pain relief achieved in a given patient. It will be well understood by those skilled in the medical art that pain measurement is highly subjective and great individual variations may occur among patients.

The terms "maintenance therapy" and "chronic therapy" are defined for purposes of the present invention as the drug therapy administered to a patient after a patient is titrated with an opioid analgesic to a steady state as defined above.

The term "minimum effective analgesic concentration" or "MEAC" with respect to concentrations of opioids such as hydrocodone is very difficult to quantify. However, there is generally a minimally effective analgesic concentration of plasma hydrocodone below which no analgesia is provided. While there is an indirect relationship between, e.g., plasma hydrocodone levels and analgesia, higher and prolonged plasma levels are generally associated with superior pain relief. There is a lag time or hysteresis, between the time of peak plasma hydrocodone levels and the time of peak drug effects. This holds true for the treatment of pain with opioid analgesics in general.

The term "mean resonance time" (MRT) is defined as the average time a drug molecule stays in the body. This calculation, which is a function of absorption, distribution and elimination, is dependent in part, on the dosage form containing the active ingredient.

For purposes of the invention, unless further specified, the term "a patient" means that the discussion (or claim) is directed to the pharmacokinetic parameters of an individual patient or subject.

The term "population of patients" means that the discussion (or claim) is directed to the mean pharmacokinetic parameters of at least two patients or subjects.

The term "breakthrough pain" means pain which the patient experiences despite the fact that the patient is being administered generally effective amounts of the sustained release solid oral dosage forms of the invention containing hydromorphone.

The term "rescue" refers to a dose of an analgesic which is administered to a patient experiencing breakthrough pain.

The term "effective pain management" means an objective evaluation of a human patient's response (pain experienced versus side effects) to analgesic treatment by a physician as well as subjective evaluation of therapeutic treatment by the patient undergoing such treatment. One skilled in the art will understand that effective analgesia will vary according to many factors, including individual patient variability.

The term "immediate release hydrocodone reference formulation" for purposes of the present invention, is an equivalent amount of the hydrocodone portion of Lortab®, (hydrocodone bitartrate and acetaminophen tablets), commercially available from UCB Pharma, Inc, or a pharmaceutical product that provides an immediate release of hydrocodone or a salt thereof.

For purposes of the invention, the controlled release formulations disclosed herein and the immediate release control formulations are dose proportional. In such formulations, the pharmacokinetic parameters (e.g. AUC and Cmax) increase linearly from one dosage strength to another. Therefore the pharmacokinetic parameters of a particular dose can be inferred from the parameters of a different dose of the same formulation.

For purposes of the invention, unless otherwise specified, the pharmacokinetic parameters disclosed herein are based on the administration of a single dose of a hydrocodone formulation to an individual patient. Pharmacokinetic parameters based on a patient population will be specified as "mean" data.

The term "first administration" means a single dose of the present invention at the initiation of therapy to an individual patient or a patient population.

The controlled-release oral solid dosage forms of the present invention surprisingly may be opioid-sparing. It is possible that the controlled-release oral solid dosage forms of the present invention may be dosed at a substantially lower daily dosage in comparison to conventional immediate-release products, with no difference in analgesic efficacy. At comparable daily dosages, greater efficacy may result with the use of the controlled-release oral solid dosage forms of the present invention in comparison to conventional immediate-release products.

BRIEF DESCRIPTION OF THE DRAWINGS

The figures attached herewith are illustrative of embodiments of the invention and are not meant to limit the scope of the invention as encompassed by the claims.

DETAILED DESCRIPTION

Figure 1:
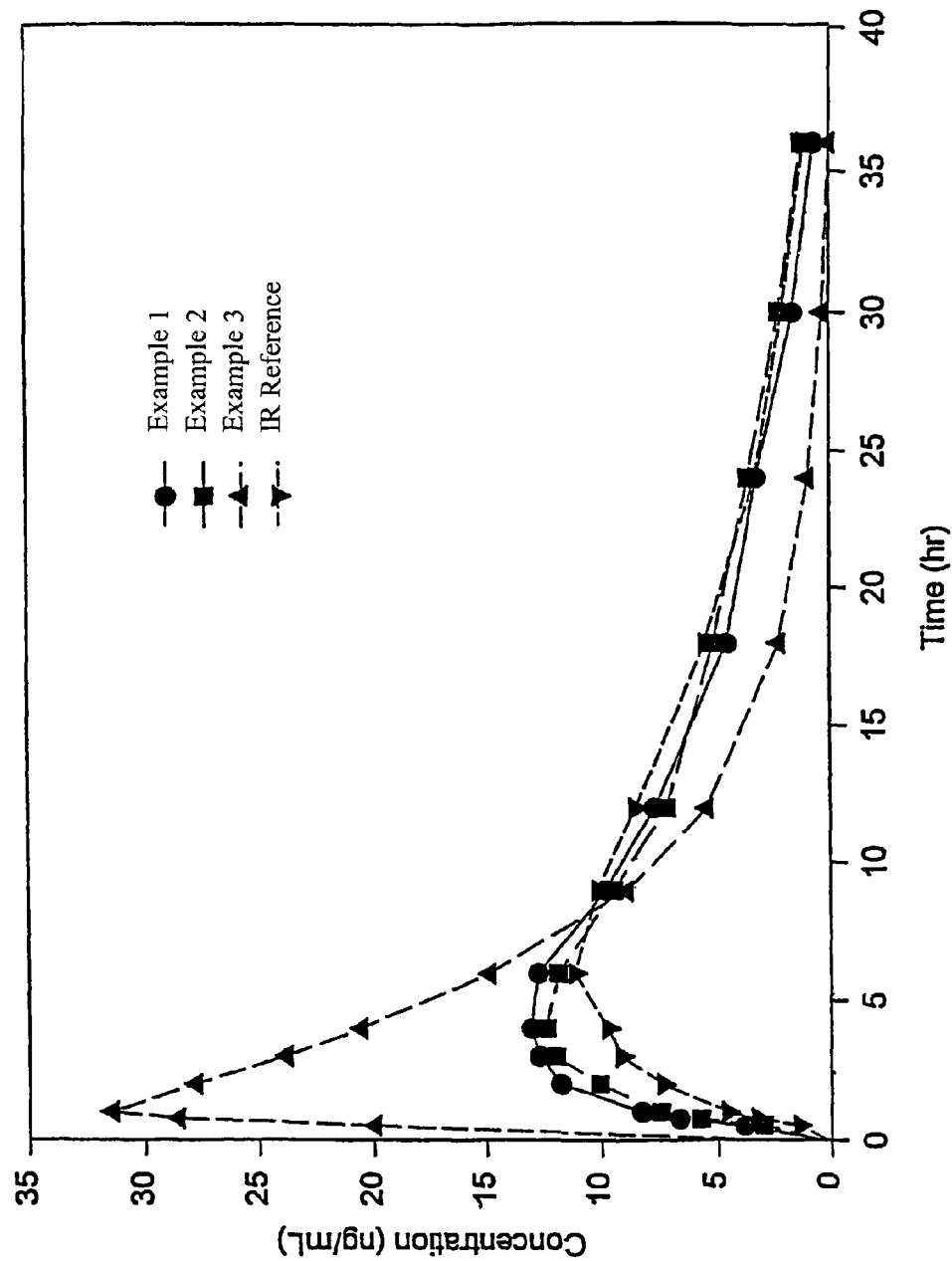
FIG. 1 is a graphical representation of the mean hydrocodone plasma concentration of Example 1, Example 2, Example 3 and an equivalent dose of immediate release hydrocodone.
Figure 2:
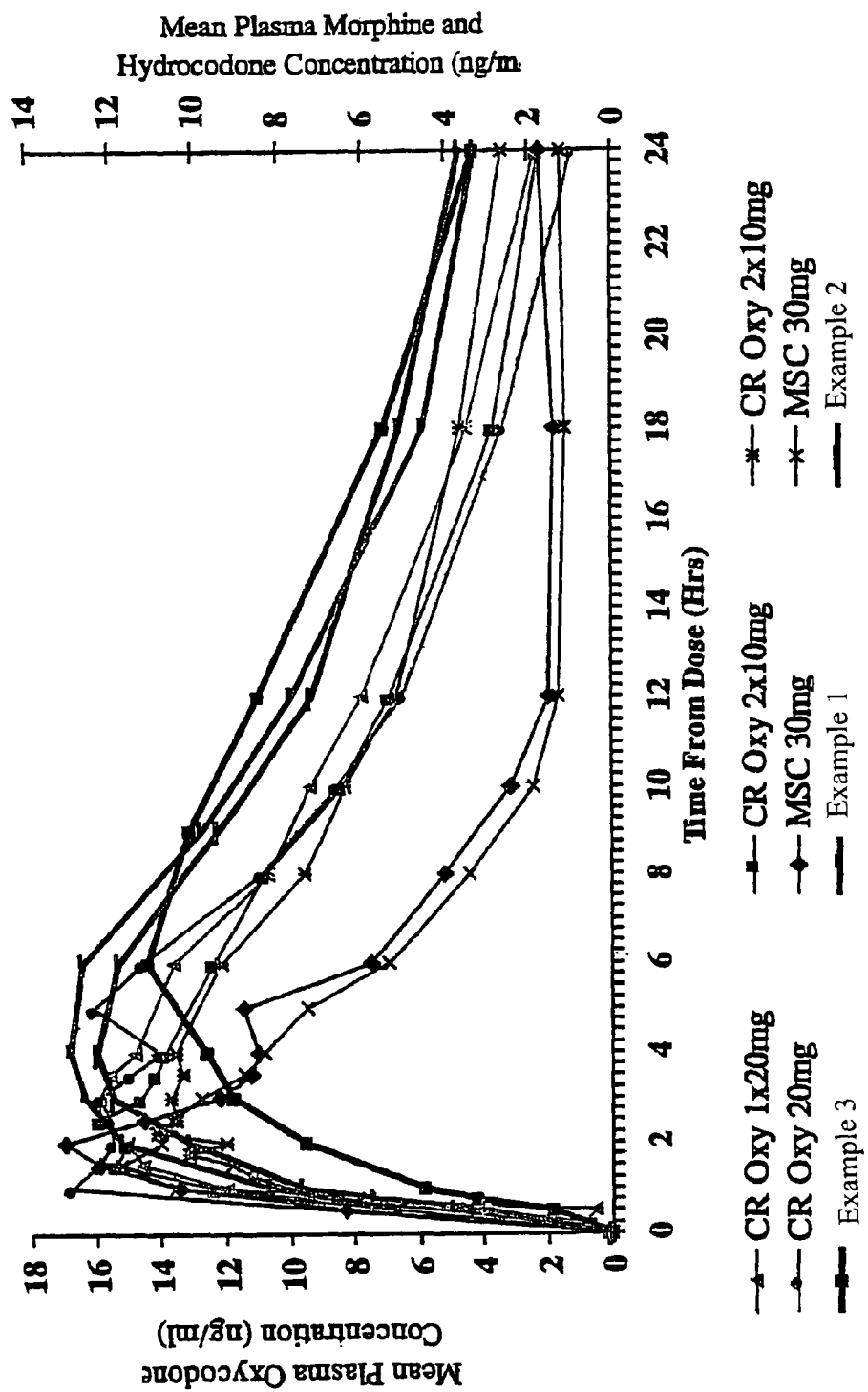
FIG. 2 is a graphical representation of the mean plasma concentration of Example 1, Example 2 and Example 3, against different samples of controlled release oxycodone manufactured in accordance with the procedures of Example 4, and different samples of controlled release morphine manufactured in accordance with the procedures of Example 5.
Figure 3:
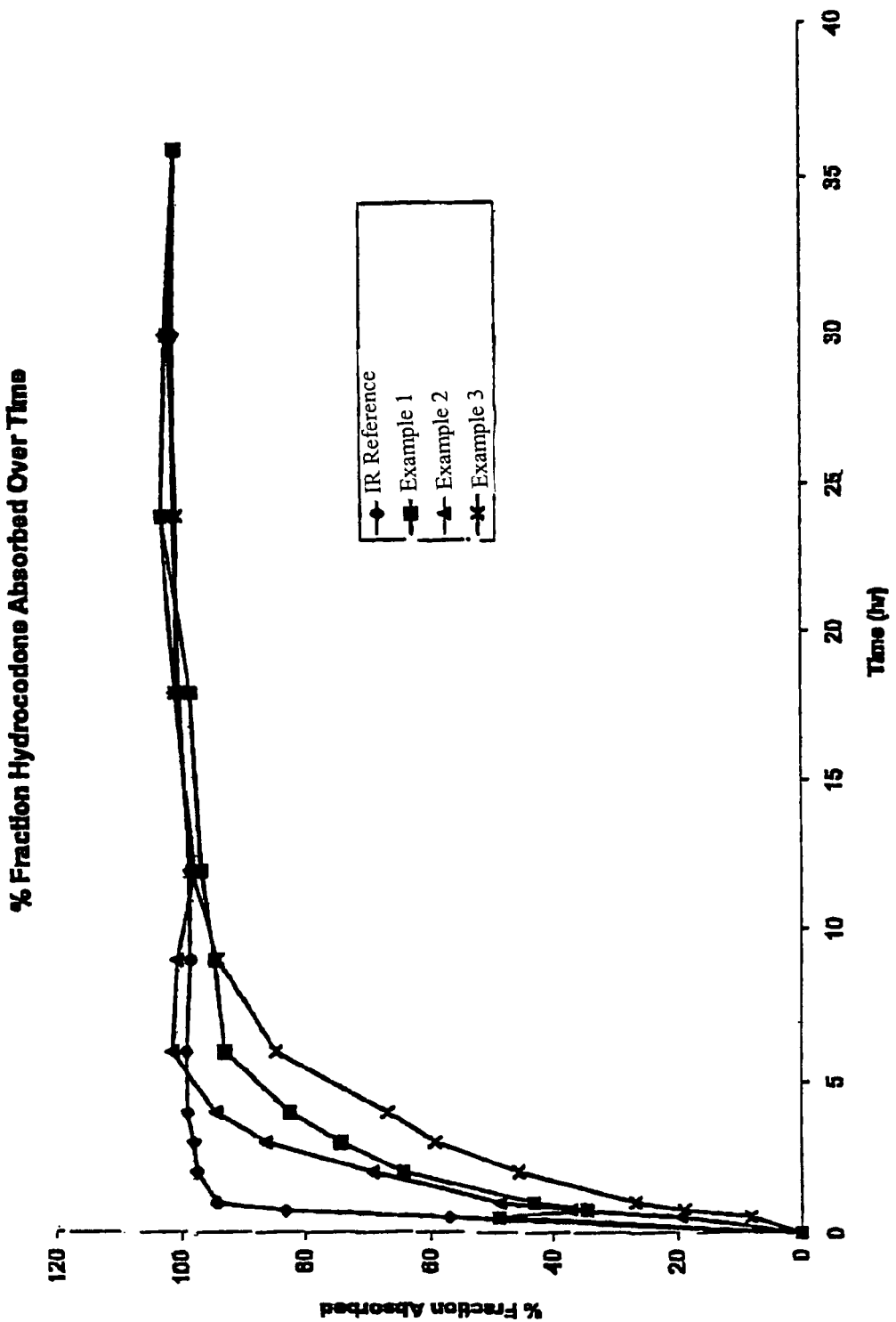
FIG. 3 is a graphical representation of the % fraction hydrocodone absorbed over time of Example 1, Example 2, Example 3 and an equivalent dose of immediate release hydrocodone.

The above embodiments of the invention can be provided by a wide variety of controlled release formulations known to those skilled in the art. For example, suitable controlled release dosage forms are disclosed in U.S. Pat. Nos. 4,861,598 and 4,970,075, hereby incorporated by reference In certain embodiments of the present invention, an effective amount of opioid in immediate release form is included in the formulation. The immediate release form of the opioid is included in an amount which is effective to shorten the time to maximum concentration of the opioid in the blood (e.g., plasma), such that the $T_{max}$ is shortened to a time of, e.g., from about 2 to about 5 hours, or from about 2 to about 4 hours. It has been discovered that by including such an effective amount of immediate release opioid in the unit dose, the experience of relatively higher levels of pain in patients is significantly reduced. In such embodiments, an effective amount of the opioid in immediate release form may be coated onto the substrates of the present invention. For example, where the extended release opioid from the formulation is due to a controlled release coating, the immediate release layer would be overcoated on top of the controlled release coating. On the other hand, the immediate release layer may be coated onto the surface of substrates wherein the opioid is incorporated in a controlled release matrix. Where a plurality of the sustained release substrates comprising an effective unit dose of the opioid (e.g., multiparticulate systems including pellets, spheres, beads and the like) are incorporated into a hard gelatin capsule, the immediate release portion of the opioid dose may be incorporated into the gelatin capsule via inclusion of the sufficient amount of immediate release opioid as a powder or granulate within the capsule. Alternatively, the gelatin capsule itself may be coated with an immediate release layer of the opioid. One skilled in the art would recognize still other alternative manners of incorporating the immediate release opioid portion into the unit dose. Such alternatives are deemed to be encompassed by the appended claims.

One advantage of the opioid dosage forms of the present invention is that therapeutic concentrations are generally achieved substantially without significant increases in the intensity and/or degree of concurrent side effects, such as nausea, vomiting, or drowsiness, which are often associated with high blood concentrations of opioids. There is also evidence to suggest that the use of the present dosage forms lead to a reduced risk of drug addiction.

Active Agent

The controlled release oral dosage forms of the present invention preferably include from about 0.5 mg to about 1250 mg hydrocodone or an equivalent amount of a pharmaceutically acceptable salt thereof. In more preferred embodiments, the dosage form can include from about 5 mg to about 60 mg, e.g. 15 mg. Suitable pharmaceutically acceptable salts of hydrocodone include hydrocodone bitartrate, hydrocodorie bitartrate hydrate, hydrocodone hydrochloride, hydrocodone p-toluenesulfonate, hydrocodone phosphate, hydrocodone thiosemicarbazone, hydrocodone sulfate, hydrocodone trifluoroacetate, hydrocodone hemipentahydrate, hydrocodone pentafluoropropionate, hydrocodone p-nitrophenylhydrazone, hydrocodone o-methyloxime, hydrocodone semicarbazone, hydrocodone hydrobromide, hydrocodone mucate, hydrocodone oleate, hydrocodone phosphate dibasic, hydrocodone phosphate monobasic, hydrocodone inorganic salt, hydrocodone organic salt, hydrocodone acetate trihydrate, hydrocodone bis(heptafuorobutyrate), hydrocodone bis(methylcarbamate), hydrocodone bis(pentafluoropropionate), hydrocodone bis(pyridine carboxylate), hydrocodone bis(trifluoroacetate), hydrocodone chlorhydrate, and hydrocodone sulfate pentahydrate. Preferably, the hydrocodone is present as the bitartrate salt.

The dosage forms of the present invention may further include one or more additional drugs which may or may not act synergistically with the hydrocodone analgesics of the present invention. Examples of such additional drugs include non-steroidal anti-inflammatory agents, including ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpmac, mefenamic acid, meclofenamic acid, flufenamic acid, niflumic acid tolfenamic acid, diflurisal, flufenisal, piroxicam, sudoxicam or isoxicam, and the like. Such non-steroidal anti-inflammatory agents also include cyclo-oxygenase inhibitors such as celecoxib —(SC-58635), DUP-697, flosulide (CGP-28238), meloxicam, 6-methoxy-2 naphthylacetic acid (6-MNA), Vioxx (MK-966), nabumetone (prodrug for 6-MNA), nimesulide, NS-398, SC-5766, SC-58215, and T-614. as amantadine (1-aminoadamantine), and memantine (3,5 dimethylaminoadamantone), their mixtures and pharmaceutically acceptable salts thereof.

Other additional drugs include nontoxic NMDA receptor antagonists such dextrorphan, dextromethorphan, 3-(1-naphthalenryl)-5-(phosphonomethyl)-L-phenylalanine, 3-(1-naphthalenyl)-5-(phosphonomethyl)-DL-phenylalanine, 1-(3,5-dimethylphenyl)naphthalene, and 2-(3,5-dimethylphenyl) naphthalene, 2SR,4RS-4-(((1H-Tetrazol-5-yl)methyl)oxy)piperidine-2-carboxylic acid; 2SR,4RS-4-((((1H-Tetrazol-5-yl)methyl)oxy)methyl)piperidine-2-carboxylic acid; E and Z 2SR-4-(O-(1H-Tetrazol-5-yl)methyl)ketoximino)piperidine-2-carboxylic acid; 2SR,4RS-4-((1H-Tetrazol-5-yl)thio)piperidine-2-carboxylic acid; 2SR,4RS-4-((1H-Tetrazol-5-yl)thio)piperidine-2-carboxylic acid; 2SR, 4RS-4-(5-mercapto-1'-Tetrazol-1-yl)piperidine-2-carboxylic acid; 2SR,4RS-4-(5-mercapto-2H-Tetrazol-2-yl)piperidine-2-carboxylic acid; 2SR,4RS-4-(5-mercapto-2H-Tetrazol-1-yl)piperidine-2-carboxylic acid; 2SR,4RS-4-(5-mercapto-2H-Tetrazol-2-yl)piperidine-2-carboxylic acid; 2SR, 4RS-4-(((1H-Tetrazol-5-yl)thio)meth yl)piperidine-2-carboxylic acid; 2SR, 4RS-4-((5-mercapto-1H-Tetrazol-5-yl)methyl)piperidine-2-carboxylic acid; or 2SR,4RS-4-((5-mercapto-2H-Tetrazol-2-yl)methyl)piperidine-2-carboxylic acid, their mixtures and pharmaceutically acceptable salts thereof.

Other suitable additional drugs which may be included in the dosage forms of the present invention include acetaminophen, aspirin, neuro-active steroids (such as those disclosed in U.S. Ser. No. 09/026,520, filed Feb. 20, 1998, hereby incorporated by reference) and other non-opioid analgesics.

For example, if a second (non-opioid) drug is included in the formulation, such drug may be included in controlled release form or in immediate release form. The additional drug may be incorporated into the controlled release matrix along with the opioid; incorporated into the controlled release coating; incorporated as a separated controlled release layer or immediate release layer; or may be incorporated as a powder, granulation, etc., in a gelatin capsule with the substrates of the present invention.

In certain preferred embodiments of the present invention, an effective amount of hydrocodone in immediate release form is included in the controlled release unit dose hydrocodone formulation to be administered. The immediate release form of the hydrocodone is included in an amount which is effective to shorten the time to Cmax of the hydrocodone in the blood (e.g., plasma). In such embodiments, an effective amount of the hydrocodone in immediate release form may be coated onto the substrates of the present invention. For example, where the extended release hydrocodone from the formulation is due to a controlled release coating, the immediate release layer would be overcoated on top of the controlled release coating. On the other hand, the immediate release layer may be coated onto the surface of substrates wherein the hydrocodone is incorporated in a controlled release matrix. Where a plurality of the sustained release substrates comprising an effective unit dose of the hydrocodone (e.g., multiparticulate systems including pellets, spheres, beads and the like) are incorporated into a hard gelatin capsule, the immediate release portion of the opioid dose may be incorporated into the gelatin capsule via inclusion of the sufficient amount of immediate release hydrocodone as a powder or granulate within the capsule. Alternatively, the gelatin capsule itself may be coated with an immediate release layer of the hydrocodone. One skilled in the art would recognize still other alternative manners of incorporating the immediate release hydromorphone portion into the unit dose. Such alternatives are deemed to be encompassed by the appended claims. It has been discovered that by including such an effective amount of immediate release hydrocodone in the unit dose, the experience of relatively higher levels of pain in patients is significantly reduced.

Dosage Forms

The controlled-release dosage form may optionally include a controlled release material which is incorporated into a matrix along with the hydrocodone, or which is applied as a sustained release coating over a substrate comprising the drug (the term "substrate" encompassing beads, pellets, spheroids, tablets, tablet cores, etc). The controlled release material may be hydrophobic or hydrophilic as desired. The oral dosage form according to the invention may be provided as, for example, granules, spheroids, pellets (hereinafter collectively referred to as "multiparticulates"). An amount of the multiparticulates which is effective to provide the desired dose of opioid over time may be placed in a capsule or may be incorporated in any other suitable oral solid form, e.g., compressed into a tablet. On the other hand, the oral dosage form according to the present invention may be prepared as a tablet core coated with a controlled-release coating, or as a tablet comprising a matrix of drug, controlled release material, and optionally other pharmaceutically desirable ingredients (e.g., diluents, binders, colorants, lubricants, etc.).

Controlled Release Matrix Formulations

In certain preferred embodiments of the present invention, the controlled-release formulation is achieved via a matrix (e.g. a matrix tablet) which includes a controlled-release material as set forth above. A dosage form including a controlled-release matrix provides in-vitro dissolution rates of the opioid within the preferred ranges and that releases the opioid in a pH-dependent or pH-independent manner. The materials suitable for inclusion in a controlled-release matrix will depend on the method used to form the matrix. The oral dosage form may contain between 1% and 80% (by weight) of at least one hydrophilic or hydrophobic controlled release material.

A non-limiting list of suitable controlled-release materials which may be included in a controlled-release matrix according to the invention include hydrophilic and/or hydrophobic materials, such as gums, cellulose ethers, acrylic resins, protein derived materials, waxes, shellac, and oils such as hydrogenated castor oil, hydrogenated vegetable oil. However, any pharmaceutically acceptable hydrophobic or hydrophilic controlled-release material which is capable of imparting controlled-release of the opioid may be used in accordance with the present invention. Preferred controlled-release polymers include alkylcelluloses such as ethylcellulose, acrylic and methacrylic acid polymers and copolymers, and cellulose ethers, especially hydroxyalkylcelluloses (especially hydroxypropylmethylcellulose) and carboxyalkylcelluloses. Preferred acrylic and methacrylic acid polymers and copolymers include methyl methacrylate, methyl methacrylate copolymers, ethoxyethyl methacrylates, cynaoethyl methacrylate, aminoalkyl methacrylate copolymer, poly(acrylic acid), poly(methacrylic acid), methacrylic acid alkylamine copolymer, poly(methyl methacrylate), poly(methacrylic acid)(anhydride), polymethacrylate, polyacrylamide, poly(methacrylic acid anhydride), and glycidyl methacrylate copolymers. Certain preferred embodiments utilize mixtures of any of the foregoing controlled-release materials in the matrices of the invention.

The matrix also may include a binder. In such embodiments, the binder preferably contributes to the controlled-release of the hydrocodone from the controlled-release matrix.

Preferred hydrophobic binder materials are water-insoluble with more or less pronounced hydrophilic and/or hydrophobic trends. Preferably, the hydrophobic binder materials useful in the invention have a melting point from about 30 to about 200° C., preferably from about 45 to about 90° C. When the hydrophobic material is a hydrocarbon, the hydrocarbon preferably has a melting point of between 25° and 90° C. Of the long chain ($C_8$-$C_{50}$) hydrocarbon materials, fatty (aliphatic) alcohols are preferred. The oral dosage form may contain up to 80% (by weight) of at least one digestible, long chain hydrocarbon.

Preferably, the oral dosage form contains up to 80% (by weight) of at least one polyalkylene glycol. Specifically, the hydrophobic binder material may comprise natural or synthetic waxes, fatty alcohols (such as lauryl, myristyl, stearyl, cetyl or preferably cetostearyl alcohol), fatty acids, including but not limited to fatty acid esters, fatty acid glycerides (mono-, di-, and tri-glycerides), hydrogenated fats, hydrocarbons, normal waxes, stearic aid, stearyl alcohol and hydrophobic and hydrophilic materials having hydrocarbon backbones. Suitable waxes include, for example, beeswax, glycowax, castor wax and carnauba wax. For purposes of the present invention, a wax-like substance is defined as any material which is normally solid at room temperature and has a melting point of from about 30 to about 100° C.

Preferred hydrophobic binder materials which may be used in accordance with the present invention include digestible, long chain ($C_8$-$C_{50}$, especially $C_{12}$-$C_{40}$), substituted or unsubstituted hydrocarbons, such as fatty acids, fatty alcohols, glyceryl esters of fatty acids, mineral and vegetable oils, natural and synthetic waxes and polyalkylene glycols. Hydrocarbons having a melting point of between 25° and 90° C. are preferred. Of the long-chain hydrocarbon binder materials, fatty (aliphatic) alcohols are preferred in certain embodiments. The oral dosage form may contain up to 80% (by weight) of at least one digestible, long chain hydrocarbon.

In certain preferred embodiments, a combination of two or more hydrophobic binder materials are included in the matrix formulations. If an additional hydrophobic binder material is included, it is preferably selected from natural and synthetic waxes, fatty acids, fatty alcohols, and mixtures of the same. Examples include beeswax, carnauba wax, stearic acid and stearyl alcohol. This list is not meant to be exclusive.

One particular suitable controlled-release matrix comprises at least one water soluble hydroxyalkyl cellulose, at least one $C_{12}$-$C_{36}$, preferably $C_{14}$-$C_{22}$, aliphatic alcohol and, optionally, at least one polyalkylene glycol. The hydroxyalkyl cellulose is preferably a hydroxy ($C_1$ to $C_6$) alkyl cellulose, such as hydroxypropylcellulose, hydroxypropylmethylcellulose and, especially, hydroxyethyl cellulose. The amount of the at least one hydroxyalkyl cellulose in the present oral dosage form will be determined, inter alia, by the precise rate of opioid release required. The aliphatic alcohol may be, for example, lauryl alcohol, myristyl alcohol or stearyl alcohol. In particularly preferred embodiments of the present oral dosage form, however, the at least one aliphatic alcohol is cetyl alcohol or cetostearyl alcohol. The amount of the aliphatic alcohol in the present oral dosage form will be determined, as above, by the precise rate of opioid release required. It will also depend on whether at least one polyalkylene glycol is present in or absent from the oral dosage form. In the absence of at least one polyalkylene glycol, the oral dosage form preferably contains between 20% and 50% (by wt) of the aliphatic alcohol. When a polyalkylene glycol is present in the oral dosage form, then the combined weight of the aliphatic alcohol and the polyalkylene glycol preferably constitutes between 20% and 50% (by wt) of the total dosage.

In one preferred embodiment, the ratio of, e.g., the at least one hydroxyalkyl cellulose or acrylic resin to the at least one aliphatic alcohol/polyalkylene glycol determines, to a consider-able extent, the release rate of the opioid from the formulation. A ratio of the hydroxyalkyl cellulose to the aliphatic alcohol/polyalkylene glycol of between 1:2 and 1:4 is preferred, with a ratio of between 1:3 and 1:4 being particularly preferred.

The polyalkylene glycol may be, for example, polypropylene glycol or, which is preferred, polyethylene glycol. The number average molecular weight of the at least one polyalkylene glycol is preferred between 1,000 and 15,000 especially between 1,500 and 12,000.

Another suitable controlled-release matrix comprises an alkylcellulose (especially ethylcellulose), a $C_{12}$ to $C_{36}$ aliphatic alcohol and, optionally, a polyalkylene glycol.

In addition to the above ingredients, a controlled-release matrix may also contain suitable quantities of other materials, e.g., diluents, lubricants, binders, granulating aids, colorants, flavorants and glidants that are conventional in the pharmaceutical art.

In order to facilitate the preparation of a solid, controlled-release oral dosage form according to this invention there is provided, in a further aspect of the present invention, a process for the preparation of a solid, controlled-release oral dosage form according to the present invention comprising incorporating opioids or a salt thereof in a controlled-release matrix. Incorporation in the matrix may be effected, for example, by (a) forming granules comprising at least one hydrophobic and/or hydrophilic material as set forth above (e.g., a water soluble hydroxyalkyl cellulose) together with the hydrocodone;

(b) mixing the at least one hydrophobic and/or hydrophilic material-containing granules with at least one $C_{12}$—$C_{36}$ aliphatic alcohol, and (c) optionally, compressing and shaping the granules.

The granules may be formed by any of the procedures well-known to those skilled in the art of pharmaceutical formulation. For example, in one preferred method, the granules may be formed by wet granulating hydroxyalkyl cellulose/opioid with water. In a particularly preferred embodiment of this process, the amount of water added during the wet granulation step is preferably between 1.5 and 5 times, especially between 1.75 and 3.5 times, the dry weight of the opioid.

The matrices of the present invention may also be prepared via a melt pellitization technique. In such circumstance, the opioid in finely divided form is combined with a binder (also in particulate form) and other optional inert ingredients, and thereafter the mixture is pelletized, e.g., by mechanically working the mixture in a high shear mixer to form the pellets (granules, spheres). Thereafter, the pellets (granules, spheres) may be sieved in order to obtain pellets of the requisite size. The binder material is preferably in particulate form and has a melting point above about 40° C. Suitable binder substances include, for example, hydrogenated castor oil, hydrogenated vegetable oil, other hydrogenated fats, fatty alcohols, fatty acid esters, fatty acid glycerides, and the like.

Controlled-release matrices can also be prepared by, e.g., melt-granulation or melt-extrusion techniques. Generally, melt-granulation techniques involve melting a normally solid hydrophobic binder material, e.g. a wax, and incorporating a powdered drug therein. To obtain a controlled release dosage form, it may be necessary to incorporate a hydrophobic controlled release material, e.g. ethylcellulose or a water-insoluble acrylic polymer, into the molten wax hydrophobic binder material. Examples of controlled-release formulations prepared via melt-granulation techniques are found, e.g., in U.S. Pat. No. 4,861,598, assigned to the Assignee of the present invention and hereby incorporated by reference in its entirety.

The additional hydrophobic binder material may comprise one or more water-insoluble wax-like thermoplastic substances possibly mixed with one or more wax-like thermoplastic substances being less hydrophobic than said one or more water-insoluble wax-like substances. In order to achieve controlled release, the individual wax-like substances in the formulation should be substantially non-degradable and insoluble in gastrointestinal fluids during the initial release phases. Useful water-insoluble wax-like binder substances may be those with a water-solubility that is lower than about 1:5,000 (w/w).

In addition to the above ingredients, a controlled release matrix may also contain suitable quantities of other materials, e.g., diluents, lubricants, binders, granulating aids, colorants, flavorants and glidants that are conventional in the pharmaceutical art in amounts up to about 50% by weight of the particulate if desired. The quantities of these additional materials will be sufficient to provide the desired effect to the desired formulation.

Specific examples of pharmaceutically acceptable carriers and excipients that may be used to formulate oral dosage forms are described in the *Handbook of Pharmaceutical Excipients*, American Pharmaceutical Association (1986), incorporated by reference herein.

The preparation of a suitable melt-extruded matrix according to the present invention may, for example, include the steps of blending the opioid analgesic, together with a controlled release material and preferably a binder material to obtain a homogeneous mixture. The homogeneous mixture is then heated to a temperature sufficient to at least soften the mixture sufficiently to extrude the same. The resulting homogeneous mixture is then extruded, e.g., using a twin-screw extruder, to form strands. The extrudate is preferably cooled and cut into multiparticulates by any means known in the art. The strands are cooled and cut into multiparticulates. The multiparticulates are then divided into unit doses. The extrudate preferably has a diameter of from about 0.1 to about 5 mm and provides controlled release of the therapeutically active agent for a time period of from about 8 to about 24 hours.

An optional process for preparing the melt extrusioned formulations of the present invention includes directly metering into an extruder a hydrophobic controlled release material, a therapeutically active agent, and an optional binder material; heating the homogenous mixture; extruding the homogenous mixture to thereby form strands; cooling the strands containing the homogeneous mixture; cutting the strands into particles having a size from about 0.1 mm to about 12 mm; and dividing said particles into unit doses. In this aspect of the invention, a relatively continuous manufacturing procedure is realized.

Plasticizers, such as those described hereinabove, may be included in melt-extruded matrices. The plasticizer is preferably included as from about 0.1 to about 30% by weight of the matrix. Other pharmaceutical excipients, e.g., talc, mono or poly saccharides, colorants, flavorants, lubricants and the like may be included in the controlled release matrices of the present invention as desired. The amounts included will depend upon the desired characteristic to be achieved.

The diameter of the extruder aperture or exit port can be adjusted to vary the thickness of the extruded strands. Furthermore, the exit part of the extruder need not be round; it can be oblong, rectangular, etc. The exiting strands can be reduced to particles using a hot wire cutter, guillotine, etc. A melt extruded multiparticulate system can be, for example, in the form of granules, spheroids or pellets depending upon the extruder exit orifice. For purposes of the present invention, the terms "melt-extruded multiparticulate(s)" and "melt-extruded multiparticulate system(s)" and "melt-extruded particles" shall refer to a plurality of units, preferably within a range of similar size and/or shape and containing one or more active agents and one or more excipients, preferably including a hydrophobic controlled release material as described herein. Preferably the melt-extruded multiparticulates will be of a range of from about 0.1 to about 12 mm in length and have a diameter of from about 0.1 to about 5 mm. In addition, it is to be understood that the melt-extruded multiparticulates can be any geometrical shape within this size range, such as, simply by way of example, beads, seeds, pellets, etc. Alternatively, the extrudate may simply be cut into desired lengths and divided into unit doses of the therapeutically active agent without the need of a spheronization step.

In one preferred embodiment, oral dosage forms are prepared that include an effective amount of melt-extruded multiparticulates within a capsule. For example, a plurality of the melt-extruded multiparticulates may be placed in a gelatin capsule in an amount sufficient to provide an effective controlled release dose when ingested and contacted by gastric fluid.

In another preferred embodiment, a suitable amount of the multiparticulate extrudate is compressed into an oral tablet using conventional tableting equipment using standard techniques. Techniques and compositions for making tablets (compressed and molded), capsules (hard and soft gelatin) and pills are also described in *Remington's Pharmaceutical Sciences*, (Arthur Osol, editor), 1553-1593 (1980), incorporated by reference herein.

In yet another preferred embodiment, the extrudate can be shaped into tablets as set forth in U.S. Pat. No. 4,957,681 (Klimesch, et. al.), described in additional detail above and hereby incorporated by reference.

Optionally, the controlled-release matrix multiparticulate systems or tablets can be coated, or the gelatin capsule can be further coated, with a controlled release coating such as the controlled release coatings described above. Such coatings preferably include a sufficient amount of hydrophobic and/or hydrophilic controlled-release material to obtain a weight gain level from about 2 to about 25 percent, although the overcoat may be greater depending upon, e.g., the physical properties of the particular opioid analgesic used and the desired release rate, among other things.

The dosage forms of the present invention may further include combinations of melt-extruded multiparticulates containing one or more opioid analgesics. Furthermore, the dosage forms can also include an amount of an immediate release therapeutically active agent for prompt therapeutic effect. The immediate release therapeutically active agent may be incorporated, e.g., as separate pellets within a gelatin capsule, or may be coated on the surface of, e.g., beads or melt extruded multiparticulates. The unit dosage forms of the present invention may also contain a combination of, e.g., controlled release beads and matrix multiparticulates to achieve a desired effect.

The controlled-release formulations of the present invention preferably slowly release the therapeutically active agent, e.g., when ingested and exposed to gastric fluids, and then to intestinal fluids. The controlled-release profile of the melt-extruded formulations of the invention can be altered, for example, by varying the amount of controlled-release material, by varying the amount of plasticizer relative to other matrix constituents, hydrophobic material, by the inclusion of additional ingredients or excipients, by altering the method of manufacture, etc.

In other embodiments of the invention, melt-extruded formulations are prepared without the inclusion of the therapeutically active agent, which is added thereafter to the extrudate. Such formulations typically will have the therapeutically active agent blended together with the extruded matrix material, and then the mixture would be tableted in order to provide a slow release formulation. Such formulations may be advantageous, for example, when the therapeutically active agent included in the formulation is sensitive to temperatures needed for softening the hydrophobic material and/or the retardant material.

Typical melt-extrusion production systems suitable for use in accordance with the present invention include a suitable extruder drive motor having variable speed and constant torque control, start-stop controls, and ammeter. In addition, the production system will include a temperature control console which includes temperature sensors, cooling means and temperature indicators throughout the length of the extruder. In addition, the production system will include an extruder such as twin-screw extruder which consists of two counter-rotating intermeshing screws enclosed within a cylinder or barrel having an aperture or die at the exit thereof. The feed materials enter through a feed hopper and are moved through the barrel by the screws and are forced through the die into strands which are thereafter conveyed such as by a continuous movable belt to allow for cooling and being directed to a pelletizer or other suitable device to render the extruded ropes into the multiparticulate system. The pelletizer can consist of rollers, fixed knife, rotating cutter and the like. Suitable instruments and systems are available from distributors such as C.W. Brabender Instruments, Inc. of South Hackensack, N.J. Other suitable apparatus will be apparent to those of ordinary skill in the art.

A further aspect of the invention is related to the preparation of melt-extruded multiparticulates as set forth above in a manner which controls the amount of air included in the extruded product. By controlling the amount of air included in the extrudate, it has been surprisingly found that the release rate of the therapeutically active agent from the, e.g., multiparticulate extrudate, can be altered significantly. In certain embodiments, it has been surprisingly found that the pH dependency of the extruded product can be altered as well.

Thus, in a further aspect of the invention, the melt-extruded product is prepared in a manner which substantially excludes air during the extrusion phase of the process. This may be accomplished, for example, by using a Leistritz extruder having a vacuum attachment. It has been surprisingly found that extruded multiparticulates prepared according to the invention using the Leistritz extruder under vacuum provides a melt-extruded product having different physical characteristics. In particular, the extrudate is substantially non-porous when magnified, e.g., using a scanning electron microscope which provides an SEM (scanning electron micrograph). Contrary to conventional thought, it has been found that such substantially non-porous formulations provide a faster release of the therapeutically active agent, relative to the same formulation prepared without vacuum. SEMs of the multiparticulates prepared using an extruder under vacuum appear very smooth, and the multiparticulates tend to be more robust than those multiparticulates prepared without vacuum. It has been observed that in at least certain formulations, the use of extrusion under vacuum provides an extruded multiparticulate product which is more pH-dependent than its counterpart formulation prepared without vacuum.

Processes for Preparing Matrix Beads

Controlled-release dosage forms according to the present invention may also be prepared as matrix beads formulations. The matrix beads include a spheronising agent and the hydrocodone.

The hydrocodone preferably comprises from about 0.01 to about 99% by weight of the matrix bead by weight. It is preferable that the hydrocodone is included as about 0.1 to about 50% by weight of the matrix bead.

Spheronising agents which may be used to prepare the matrix bead formulations of the present invention include any art-known spheronising agent. Cellulose derivatives are preferred, and microcrystalline cellulose is especially preferred. A suitable microcrystalline cellulose is, for example, the material sold as Avicel PH 101 (Trade Mark, FMC Corporation). The spheronising agent is preferably included as about 1 to about 99% of the matrix bead by weight.

In addition to the active ingredient and spheronizing agent, the spheroids may also contain a binder. Suitable binders, such as low viscosity, water soluble polymers, will be well known to those skilled in the pharmaceutical art. However, water soluble hydroxy lower alkylcellulose, such as hydroxypropylcellulose, are preferred.

In addition to the opioid analgesic and spheronising agent, the matrix bead formulations of the present invention may include a controlled release material such as those described hereinabove. Preferred controlled-release materials for inclusion in the matrix bead formulations include acrylic and methacrylic acid polymers or copolymers, and ethylcellulose. When present in the formulation, the controlled-release material will be included in amounts of from about 1 to about 80% of the matrix bead, by weight. The controlled-release material is preferably included in the matrix bead formulation in an amount effective to provide controlled release of the opioid analgesic from the bead.

Pharmaceutical processing aids such as binders, diluents, and the like may be included in the matrix bead formulations. Amounts of these agents included in the formulations will vary with the desired effect to be exhibited by the formulation.

The matrix beads may be overcoated with a controlled-release coating including a controlled-release material such as those described hereinabove. The controlled-release coating is applied to a weight gain of from about 5 to about 30%. The amount of the controlled-release coating to be applied will vary according to a variety of factors, e.g., the composition of the matrix bead and the chemical and/or physical properties of the opioid analgesic (i.e., hydrocodone).

Matrix beads are generally prepared by granulating the spheronising agent together with the opioid analgesic, e.g. by wet granulation. The granulate is then spheronized to produce the matrix beads. The matrix beads are then optionally overcoated with the controlled release coating by methods such as those described hereinabove.

Another method for preparing matrix beads, for example, by (a) forming granules comprising at least one water soluble hydroxyalkyl cellulose and opioid or an opioid salt; (b) mixing the hydroxyalkyl cellulose containing granules with at least one $C_{12}$-$C_{36}$ aliphatic alcohol; and (c) optionally, compressing and shaping the granules. Preferably, the granules are formed by wet granulating the hydroxyalkyl cellulose/opioid with water. In a particularly preferred embodiment of this process, the amount of water added during the wet granulation step is preferably between 1.5 and 5 times, especially between 1.75 and 3.5 times, the dry weight of the opioid.

In yet other alternative embodiments, a spheronizing agent, together with the active ingredient can be spheronized to form spheroids. Microcrystalline cellulose is preferred. A suitable microcrystalline cellulose is, for example, the material sold as Avicel PH 101 (Trade Mark, FMC Corporation). In such embodiments, in addition to the active ingredient and spheronizing agent, the spheroids may also contain a binder. Suitable binders, such as low viscosity, water soluble polymers, will be well known to those skilled in the pharmaceutical art. However, water soluble hydroxy lower alkyl cellulose, such as hydroxy propyl cellulose, are preferred. Additionally (or alternatively) the spheroids may contain a water insoluble polymer, especially an acrylic polymer, an acrylic copolymer, such as a methacrylic acid-ethyl acrylate copolymer, or ethyl cellulose. In such embodiments, the sustained-release coating will generally include a water insoluble material such as (a) a wax, either alone or in admixture with a fatty alcohol; or (b) shellac or zein.

Controlled Release Bead Formulations

In one especially preferred embodiment, the oral dosage form comprises an effective number of controlled release spheroids contained within a gelatin capsule.

In another preferred embodiment of the present invention, the controlled-release dosage form comprises spheroids containing the active ingredient coated with a controlled-release coating including a controlled release material. The term spheroid is known in the pharmaceutical art and means, e.g., a spherical granule having a diameter of between 0.1 mm and 2.5 mm, especially between 0.5 mm and 2 mm.

The spheroids are preferably film coated with a controlled release material that permits release of the opioid (or salt) at a controlled rate in an aqueous medium. The film coat is chosen so as to achieve, in combination with the other stated properties, the in-vitro release rate outlined above (e.g., at least about 12.5% released after 1 hour). The controlled-release coating formulations of the present invention preferably produce a strong, continuous film that is smooth and elegant, capable of supporting pigments and other coating additives, non-toxic, inert, and tack-free.

Coatings

The dosage forms of the present invention may optionally be coated with one or more coatings suitable for the regulation of release or for the protection of the formulation. In one embodiment, coatings are provided to permit either pH-dependent or pH-independent release, e.g., when exposed to gastrointestinal fluid. When a pH-independent coating is desired, the coating is designed to achieve optimal release regardless of pH-changes in the environmental fluid, e.g., the GI tract. Other preferred embodiments include a pH-dependent coating that releases the opioid in desired areas of the gastro-intestinal (GI) tract, e.g., the stomach or small intestine, such that an absorption profile is provided which is capable of providing at least about twelve hour and preferably up to twenty-four hour analgesia to a patient. It is also possible to formulate compositions which release a portion of the dose in one desired area of the GI tract, e.g., the stomach, and release the remainder of the dose in another area of the GI tract, e.g., the small intestine.

Formulations according to the invention that utilize pH-dependent coatings may also impart a repeat-action effect whereby unprotected drug is coated over an enteric coat and is released in the stomach, while the remainder, being protected by the enteric coating, is released further down the gastrointestinal tract. Coatings which are pH-dependent may be used in accordance with the present invention include a controlled release material such as, e.g., shellac, cellulose acetate phthalate (CAP), polyvinyl acetate phthalate (PVAP), hydroxypropyl methylcellulose phthalate, and methacrylic acid ester copolymers, zein, and the like.

In another preferred embodiment, the present invention is related to a stabilized solid controlled dosage form comprising an opioid coated with a hydrophobic controlled release material selected from (i) an alkylcellulose; (ii) an acrylic polymer; or (iii) mixtures thereof. The coating may be applied in the form of an organic or aqueous solution or dispersion.

In certain preferred embodiments, the controlled release coating is derived from an aqueous dispersion of the hydrophobic controlled release material. The coated substrate containing the opioid(s) (e.g., a tablet core or inert pharmaceutical beads or spheroids) is then cured until an endpoint is reached at which the substrate provides a stable dissolution. The curing endpoint may be determined by comparing the dissolution profile (curve) of the dosage form immediately after curing to the dissolution profile (curve) of the dosage form after exposure to accelerated storage conditions of, e.g., at least one month at a temperature of 40° C. and a relative humidity of 75%. These formulations are described in detail in U.S. Pat. Nos. 5,273,760 and 5,286,493, assigned to the Assignee of the present invention and hereby incorporated by reference. Other examples of controlled-release formulations and coatings which may be used in accordance with the present invention include Assignee's U.S. Pat. Nos. 5,324,351; 5,356,467, and 5,472,712, hereby incorporated by reference in their entirety.

In preferred embodiments, the controlled release coatings include a plasticizer such as those described herein below.

In certain embodiments, it is necessary to overcoat the substrate comprising the opioid analgesic with a sufficient amount of the aqueous dispersion of e.g., alkylcellulose or acrylic polymer, to obtain a weight gain level from about 2 to about 50%, e.g., about 2 to about 25% in order to obtain a controlled-release formulation. The overcoat may be lesser or greater depending upon the physical properties of the therapeutically active agent and the desired release rate, the inclusion of plasticizer in the aqueous dispersion and the manner of incorporation of the same, for example.

Alkylcellulose Polymers

Cellulosic materials and polymers, including alkylcelluloses are controlled release materials well suited for coating the substrates, e.g., beads, tablets, etc. according to the invention. Simply by way of example, one preferred alkylcellulosic polymer is ethylcellulose, although the artisan will appreciate that other cellulose and/or alkylcellulose polymers may be readily employed, singly or on any combination, as all or part of a hydrophobic coatings according to the invention.

One commercially-available aqueous dispersion of ethylcellulose is Aquacoat® (FMC Corp., Philadelphia, Pa., U.S.A.). Aquacoat® is prepared by dissolving the ethylcellulose in a water-immiscible organic solvent and then emulsifying the same in water in the presence of a surfactant and a stabilizer. After homogenization to generate submicron droplets, the organic solvent is evaporated under vacuum to form a pseudolatex. The plasticizer is not incorporated in the pseudolatex during the manufacturing phase. Thus, prior to using the same as a coating, it is necessary to intimately mix the Aquacoat® with a suitable plasticizer prior to use.

Another aqueous dispersion of ethylcellulose is commercially available as Surelease® (Colorcon, Inc., West Point, Pa., U.S.A.). This product is prepared by incorporating plasticizer into the dispersion during the manufacturing process. A hot melt of a polymer, plasticizer (dibutyl sebacate), and stabilizer (oleic acid) is prepared as a homogeneous mixture, which is then diluted with an alkaline solution to obtain an aqueous dispersion which can be applied directly onto substrates.

Acrylic Polymers

In other preferred embodiments of the present invention, the controlled release material comprising the controlled-release coating is a pharmaceutically acceptable acrylic polymer, including but not limited to acrylic acid and methacrylic acid copolymers, methyl methacrylate copolymers, ethoxyethyl methacrylates, cynaoethyl methacrylate, poly(acrylic acid), poly(methacrylic acid), methacrylic acid alkylamide copolymer, poly(methyl methacrylate), polymethacrylate, poly(methyl methacrylate) copolymer, polyacrylarmide, aminoalkyl methacrylate copolymer, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In order to obtain a desirable dissolution profile, it may be necessary to incorporate two or more ammonio methacrylate copolymers having differing physical properties, such as different molar ratios of the quaternary ammonium groups to the neutral (meth)acrylic esters.

Certain methacrylic acid ester-type polymers are useful for preparing pH-dependent coatings which may be used in accordance with the present invention. For example, there are a family of copolymers synthesized from diethylaminoethyl methacrylate and other neutral methacrylic esters, also known as methacrylic acid copolymer or polymeric methacrylates, commercially available as Eudragit® from Rohm Tech, Inc. There are several different types of Eudragit®. For example, Eudragit E is an example of a methacrylic acid copolymer which swells and dissolves in acidic media. Eudragit L is a methacrylic acid copolymer which does not swell at about pH<5.7 and is soluble at about pH>6. Eudragit S does not swell at about pH<6.5 and is soluble at about pH>7. Eudragit RL and Eudragit RS are water swellable, and the amount of water absorbed by these polymers is pH-dependent, however, dosage forms coated with Eudragit RL and RS are pH-independent.

In certain preferred embodiments, the acrylic coating comprises a mixture of two acrylic resin lacquers commercially available from Rohm Pharma under the Tradenames Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. The code designations RL (high permeability) and RS (low permeability) refer to the permeability properties of these agents. Eudragit® RL/RS mixtures are insoluble in water and in digestive fluids. However, coatings formed from the same are swellable and permeable in aqueous solutions and digestive fluids.

The Eudragit® RL/RS dispersions of the present invention may be mixed together in any desired ratio in order to ultimately obtain a controlled-release formulation having a desirable dissolution profile. Desirable controlled-release formulations may be obtained, for instance, from a retardant coating derived from 100% Eudragit® RL, 50% Eudragit® RL and 50% Eudragit® RS, and 10% Eudragit® RL:Eudragit® 90% RS. Of course, one skilled in the art will recognize that other acrylic polymers may also be used, such as, for example, Eudragit® L.

Plasticizers

In embodiments of the present invention where the coating comprises an aqueous dispersion of a hydrophobic controlled release material, the inclusion of an effective amount of a plasticizer in the aqueous dispersion of hydrophobic material will further improve the physical properties of the controlled-release coating. For example, because ethylcellulose has a relatively high glass transition temperature and does not form flexible films under normal coating conditions, it is preferable to incorporate a plasticizer into an ethylcellulose coating containing controlled-release coating before using the same as a coating material. Generally, the amount of plasticizer included in a coating solution is based on the concentration of the film-former, e.g., most often from about 1 to about 50 percent by weight of the film-former. Concentration of the plasticizer, however, can only be properly determined after careful experimentation with the particular coating solution and method of application.

Examples of suitable plasticizers for ethylcellulose include water insoluble plasticizers such as dibutyl sebacate, diethyl phthalate, triethyl citrate, tibutyl citrate, and triacetin, although it is possible that other water-insoluble plasticizers (such as acetylated monoglycerides, phthalate esters, castor oil, etc.) may be used. Triethyl citrate is an especially preferred plasticizer for the aqueous dispersions of ethyl cellulose of the present invention.

Examples of suitable plasticizers for the acrylic polymers of the present invention include, but are not limited to citric acid esters such as triethyl citrate NF XVI, tributyl citrate, dibutyl phthalate, and possibly 1,2-propylene glycol. Other plasticizers which have proved to be suitable for enhancing the elasticity of the films formed from acrylic films such as Eudragit® RL/RS lacquer solutions include polyethylene glycols, propylene glycol, diethyl phthalate, castor oil, and triacetin. Triethyl citrate is an especially preferred plasticizer for the aqueous dispersions of ethyl cellulose of the present invention.

It has further been found that the addition of a small amount of talc to the controlled release coating reduces the tendency of the aqueous dispersion to stick during processing, and acts as a polishing agent.

Preparation of Coated Bead Formulations

When an aqueous dispersion of hydrophobic material is used to coat substrates, e.g., inert pharmaceutical beads such as nu pariel 18/20 beads, a plurality of the resultant stabilized solid controlled-release beads may thereafter be placed in a gelatin capsule in an amount sufficient to provide an effective controlled-release dose when ingested and contacted by an environmental fluid, e.g., gastric fluid or dissolution media.

The stabilized controlled-release bead formulations of the present invention slowly release the opioid analgesic, e.g., when ingested and exposed to gastric fluids, and then to intestinal fluids. The controlled-release profile of the formulations of the invention can be altered, for example, by varying the amount of overcoating with the aqueous dispersion of hydrophobic controlled release material, altering the manner in which the plasticizer is added to the aqueous dispersion of hydrophobic controlled release material, by varying the amount of plasticizer relative to hydrophobic controlled release material, by the inclusion of additional ingredients or excipients, by altering the method of manufacture, etc. The dissolution profile of the ultimate product may also be modified, for example, by increasing or decreasing the thickness of the controlled release coating.

Substrates coated with a therapeutically active agent are prepared, e.g. by dissolving the therapeutically active agent in water and then spraying the solution onto a substrate, for example, nu pariel 18/20 beads, using a Wuster insert. Optionally, additional ingredients are also added prior to coating the beads in order to assist the binding of the opioid to the beads, and/or to color the solution, etc. For example, a product which includes hydroxypropyl methylcellulose, etc. with or without colorant (e.g., Opadry®, commercially available from Colorcon, Inc.) may be added to the solution and the solution mixed (e.g., for about 1 hour) prior to application of the same onto the substrate. The resultant coated substrate may then be optionally overcoated with a barrier agent, to separate the therapeutically active agent from the hydrophobic controlled-release coating.

An example of a suitable barrier agent is one which comprises hydroxypropyl methylcellulose. However, any film-former known in the art may be used. It is preferred that the barrier agent does not affect the dissolution rate of the final product.

The substrates may then be overcoated with an aqueous dispersion of the hydrophobic controlled release material. The aqueous dispersion of hydrophobic controlled release material preferably further includes an effective amount of plasticizer, e.g. triethyl citrate. Pre-formulated aqueous dispersions of ethylcellulose, such as Aquacoat® or Surelease®, may be used. If Surelease® is used, it is not necessary to separately add a plasticizer. Alternatively, preformulated aqueous dispersions of acrylic polymers such as Eudragit® can be used.

The coating solutions of the present invention preferably contain, in addition to the film-former, plasticizer, and solvent system (i.e., water), a colorant to provide elegance and product distinction. Color may be added to the solution of the therapeutically active agent instead, or in addition to the aqueous dispersion of hydrophobic material. For example, color can be added to Aquacoat® via the use of alcohol or propylene glycol based color dispersions, milled aluminum lakes and opacifiers such as titanium dioxide by adding color with shear to water soluble polymer solution and then using low shear to the plasticized Aquacoat®. Alternatively, any suitable method of providing color to the formulations of the present invention may be used. Suitable ingredients for providing color to the formulation when an aqueous dispersion of an acrylic polymer is used include titanium dioxide and color pigments, such as iron oxide pigments. The incorporation of pigments, may, however, increase the retard effect of the coating.

The plasticized aqueous dispersion of hydrophobic controlled release material may be applied onto the substrate comprising the therapeutically active agent by spraying using any suitable spray equipment known in the art. In a preferred method, a Wurster fluidized-bed system is used in which an air jet, injected from underneath, fluidizes the core material and effects drying while the acrylic polymer coating is sprayed on. A sufficient amount of the aqueous dispersion of hydrophobic material to obtain a predetermined controlled-release of said therapeutically active agent when said coated substrate is exposed to aqueous solutions, e.g. gastric fluid, is preferably applied, taking into account the physical characteristics of the therapeutically active agent, the manner of incorporation of the plasticizer, etc. After coating with the hydrophobic controlled release material, a further overcoat of a film-former, such as Opadry®, is optionally applied to the beads. This overcoat is provided, if at all, in order to substantially reduce agglomeration of the beads.

The release of the therapeutically active agent from the controlled-release formulation of the present invention can be further influenced, i.e., adjusted to a desired rate, by the addition of one or more release-modifying agents, or by providing one or more passageways through the coating. The ratio of hydrophobic controlled release material to water soluble material is determined by, among other factors, the release rate required and the solubility characteristics of the materials selected.

The release-modifying agents which function as pore-formers may be organic or inorganic, and include materials that can be dissolved, extracted or leached from the coating in the environment of use. The pore-formers may comprise one or more hydrophilic materials such as hydroxypropylmethylcellulose.

The controlled-release coatings of the present invention can also include erosion-promoting agents such as starch and gums.

The controlled-release coatings of the present invention can also include materials useful for making microporous lamina in the environment of use, such as polycarbonates comprised of linear polyesters of carbonic acid in which carbonate groups reoccur in the polymer chain.

The release-modifying agent may also comprise a semipermeable polymer. In certain preferred embodiments, the release-modifying agent is selected from hydroxypropylmethylcellulose, lactose, metal stearates, and mixtures of any of the foregoing.

The controlled-release coatings of the present invention may also include an exit means comprising at least one passageway, orifice, or the like. The passageway may be formed by such methods as those disclosed in U.S. Pat. Nos. 3,845,770; 3,916,889; 4,063,064; and 4,088,864, all of which are hereby incorporated by reference. The passageway can have any shape such as round, triangular, square, elliptical, irregular, etc.

Another method of producing controlled release bead formulations suitable for about 24-hour administration is via powder layering. U.S. Pat. No. 5,411,745, assigned to the Assignee of the present invention and hereby incorporated by reference in its entirety, teaches preparation of 24-hour morphine formulations prepared via powder layering techniques utilizing a processing aid consisting essentially of hydrous lactose impalpable. The powder-layered beads are prepared by spraying an aqueous binder solution onto inert beads to provide a tacky surface, and subsequently spraying a powder that is a homogenous mixture of morphine sulfate and hydrous lactose impalpable onto the tacky beads. The beads are then dried and coated with a hydrophobic material such as those described hereinabove to obtain the desired release of drug when the final formulation is exposed to environmental fluids. An appropriate amount of the controlled release beads are then, e.g. encapsulated to provide a final dosage form which provides effective plasma concentrations of morphine for about 12 hours.

DETAILED DESCRIPTION OF THE PREFERRED EMBODIMENTS

The following examples illustrate various aspects of the present invention. They are not meant to be construed to limit the claims in any manner whatsoever.

Example 1

Hydrocodone sustained release tablets were produced with the formula set forth in Table 1 below:

TABLE 1

| Ingredients | Amt/Unit (mg) | Amount/Batch (gm) |
| --- | --- | --- |
| Hydrocodone Bitartrate | 15.0 | 150.0 |
| Spray Dried Lactose | 56.0 | 560.0 |
| Povidone | 4.0 | 40.0 |
| Eudragit RS30D (solids) | 10.0 | 100.0 |
| Triacetin | 2.0 | 20.0 |
| Stearyl Alcohol | 20.0 | 200.0 |

TABLE 1-continued

| Ingredients | Amt/Unit (mg) | Amount/Batch (gm) |
|---|---|---|
| Talc | 2.0 | 20.0 |
| Magnesium Stearate | 1.0 | 10.0 |
| Total | 110.0 | 1100.0 |

According to the following procedure:
1. Retardant dispersion: Blend Eudragit RS30D and Triacetin using a lightnin mixer.
2. Melt Stearyl Alcohol.
3. Spray retardant dispersion onto Hydrocodone Bitartrate, Spray Dried Lactose, and Povidone using a fluid bed granulator.
4. Dry batch on a stainless steel tray for 15 minutes, or till constant weight.
5. Incorporate the melted Stearyl Alcohol into the batch using a Hobart mixer.
6. Dry waxed granulation on a stainless steel tray for 30 minutes, or temperature of granulation reaches 35° C. or less.
7. Mill the cooled granulation through a CoMil.
8. Lubricate the granulation with talc and magnesium stearate using a Hobart Mixer.
9. Compress the granulation into tablets using a tablet press.

The Tablets were then tested for dissolution using the following procedure:
1. Apparatus: USP Method I (basket), 100 rpm.,
2. Medium: 700 ml SGF for 55 min, thereafter 900 ml of SIF without enzyme
3. Sampling time: 1, 2, 4, 8 and 12 hours.
4. Analytical: High Performance Liquid Chromatography.

The dissolution parameters are set forth in Table II below:

TABLE II

| Time (Hours) | % Dissolved |
|---|---|
| 1 | 39.7 |
| 2 | 51.5 |
| 4 | 67.4 |
| 8 | 86.4 |
| 12 | 96.1 |

The Cmax and Tmax were then obtained for Example 1 and an immediate release reference standard in a bioavailability study comparing hydrocodone 15 mg administered as an immediate release formulation (Lortab 7.5 mg X 2) to the above CR formulation in healthy human subjects, as set forth in Table III below:

TABLE III

| Pharmacokinetic data | Hydrocodone Bitartrate |
|---|---|
| Cmax (ng/ml) IR reference product | 35.4 |
| Cmax (ng/ml) CR product | 13.4 |
| Cmax (CR)/Cmax (IR) | 38% |
| Tmax (hr) IR reference product | 1.32 |
| Tmax (hr) CR product | 4.07 |

Example 2

Hydocodone sustained release tablets were produced with the formula set forth in Table IV below:

TABLE IV

| Ingredients | Amt/Unit (mg) | Amt/Batch (g) |
|---|---|---|
| Hydrocodone Bitartrate | 15.0 | 150.0 |
| Spray Dried Lactose | 51.0 | 510.0 |
| Povidone | 4.0 | 40.0 |
| Eudragit RS30D (solids) | 10.0 | 100.0 |
| Triacetin | 2.0 | 20.0 |
| Stearyl Alcohol | 25.0 | 250.0 |
| Talc | 2.0 | 20.0 |
| Magnesium Stearate | 1.0 | 10.0 |
| Total | 110.0 | 1100.0 | according to the procedure of Example 1.

The dissoultion parameters were then obtained using the procedure of Example 1. The results are set forth in Table V below:

TABLE V

| Time (Hours) | % Dissolved |
|---|---|
| 1 | 36 |
| 2 | 45.8 |
| 4 | 60.5 |
| 8 | 78.9 |
| 12 | 90.4 |

Example 3

Hydocodone sustained release capsules were produced with the formula set forth in Table VI below:

TABLE VI

| Ingredients | Amt/Unit (mg) | Amt/Batch (g) |
|---|---|---|
| Hydrocodone Bitartrate | 15.0 | 320.0 |
| Eudragit RSPO | 76.0 | 1520.0 |
| Eudragit RLPO | 4.0 | 80.0 |
| Stearyl Alcohol | 25.0 | 500.0 |
| Total | 120.0 | 2400.0 |

According to the following procedure:
1. Blend milled Stearyl Alcohol, Eudragit RLPO, Hydrocodone Bitartrate, and Eudragit RSPO using a Hobart Mixer.
2. Extrude the granulation using a Powder Feeder, Melt Extruder (equipped with the 6×1 mm die head), Conveyor Lasermike, and Pelletizer under the following conditions:

| Zone 1 | 10° C. |
|---|---|
| Zone 2 | 20° C. |
| Zone 3 | 120° C. |
| Zone 4 | 120° C. |
| Zone 5 | 120° C. |
| Zone 6 | 120° C. |
| Zone 7 | 95° C. |

-continued

| | |
|---|---|
| Zone 8 | 95° C. |
| MGA | 120° C. |
| Die | 117° C. |

Powder feed rate-40 g/min; screw speed-185 rpm; vacuum-~980 mBar
Conveyor-such that diameter of exrudate is 1 mm
Pelletizzer-such that pellets are cut to 1 mm in length
3. Screen pellets using #16 and #20 mesh screens. Collect material that passes through the #16 mesh screen and is retained on the #20 mesh screen.
4. Fill size #2 clear gelatin capsules with the pellets. Range: NLT 114 mg and NMT 126

The dissolution parameters were then obtained using the procedure of Example 1. The results are set forth in Table VII below:

TABLE VII

| Time (Hours) | % Dissolved |
|---|---|
| 1 | 23.9 |
| 2 | 34.7 |
| 4 | 51.7 |
| 8 | 74.6 |
| 12 | 85.2 |

Example 4

Oxycodone sustained release tablets were produced with the formula set forth in Table VII below:

TABLE VIII

| Ingredients | Amt/Unit (mg) | Amount/Batch (gm) |
|---|---|---|
| Oxycodone HCl | 20.0 | 22.0 |
| Spray Dried Lactose | 59.25 | 65.175 |
| Povidone | 5.0 | 5.5 |
| Eudragit RS30D (solids) | 10.0 | 11.0 |
| Triacetin | 2.0 | 2.2 |
| Stearyl Alcohol | 25.0 | 27.5 |
| Talc | 2.5 | 2.75 |
| Magnesium Stearate | 1.25 | 1.375 |
| Opadry Pink Y-S-14518A | 4.0 | 4.26 |
| Total | 129.0 | 141.76 |

According to the following procedure:
1. Granulation: Spray the Eudragit/Triacetin dispersion onto the Oxycodone HCl, Spray Dried Lactose and Povidone using a fluid bed granulator.
2. Milling: Discharge the granulation and pass through a mill.
3. Waxing: Melt the stearyl alcohol and add to the milled granulation using a mixer. Allow to cool.
4. Milling: Pass the cooled granulation through a mill.
5. Lubrication: Lubricate the granulation with talc and magnesium stearate using a mixer.
6. Compression: Compress the granulation into tablets using a tablet press.
7. Film Coating: Apply an aqueous film coat to the tablets.

The tablets were then tested for dissolution using the following procedure:
1. Apparatus: USP Type II (paddle), 150 rpm.
2. Medium: 700 ml SGF for first hour, thereafter made 900 ml with phosphate buffer to pH 7.5.
3. Sampling time: 1, 2, 4, 8, 12, 18 and 24 hours.
4. Analytical: High Performance Liquid Chromatography.

The dissolution parameters are set forth in Table IX below:

TABLE IX

| Time (hrs) | % Dissolved |
|---|---|
| 1 | 45 |
| 2 | 55 |
| 4 | 70 |
| 8 | 87 |
| 12 | 96 |
| 18 | 101 |
| 24 | 102 |

The Cmax and Tmax were then obtained for Example 4 and an immediate release reference standard in a bioavailability study, as set forth in Table X below:

TABLE X

| Pharmacokinetic data | Oxycodone HCl |
|---|---|
| Cmax (ng/ml) IR reference product | 38.2 |
| Cmax (ng/ml) CR product | 21.7 |
| Cmax (CR)/Cmax (IR) | 57% |
| Tmax (hr) IR reference product | 1.10 |
| Tmax (hr) CR product | 2.62 |

Example 5

Morphine sustained release tablets were produced with the formula set forth in Table XI below:

TABLE XI

| Ingredients | Amount/unit (mg) | Amount/batch (kg) |
|---|---|---|
| Morphine sulfate | 30.0 | 138.0 |
| Spray Dried Lactose | 70.0 | 322.0 |
| Hydroxyethyl cellulose | 10.0 | 46.0 |
| Cetostearyl alcohol | 35.0 | 161.0 |
| Talc | 3.0 | 13.8 |
| Magnesium stearate | 2.0 | 9.2 |
| Opadry YS-1-4729 | 5.0 | 23.0 |
| To0tal | 155.0 | 713.0 |

According to the following procedure:
1. Granulation: Add water to the Morphine sulfate, Spray Dried Lactose and Hydroxyethyl cellulose in a mixer and dry using a fluid bed granulator.
2. Screening: Discharge the granulation and pass through a sieve.
3. Waxing: Melt the cetostearyl alcohol and add to the milled granulation using a mixer. Allow to cool.
4. Screening: Pass the cooled granulation through a sieve.
5. Lubrication: Lubricate the granulation with talc and magnesium stearate using a mixer.
6. Compression: Compress the granulation into tablets using a tablet press.
7. Film coating: Apply an aqueous film coat to the tablets.

The tablets were then tested for dissolution using the following procedure:
1. Apparatus: USP Method I (Basket), 50 rpm
2. Medium: 900 ml of Purified Water, 37° C.
3. Sampling time: 1, 2, 3, 4, and 6 hours.
4. Analytical: UV detection, 285 nm and 305 nm, 2-point method using 5-cm cell.

The dissolution parameters are set forth in Table XII below:

TABLE XII

| Time (Hours) | % Dissolved |
|---|---|
| 1 | 34.2 |
| 2 | 49.9 |
| 3 | 64.2 |
| 4 | 75.5 |
| 6 | 90.3 |

The Cmax and Tmax were then obtained for Example 5 and an immediate release reference standard in a bioavailability study, as set forth in Table XIII below:

TABLE XIII

| Pharmacokinetic data | Morphine Sulphate |
|---|---|
| Cmax (ng/ml) IR reference product | 22.1 |
| Cmax (ng/ml) CR product | 12 |
| Cmax (CR)/Cmax (IR) | 54% |
| Tmax (hr) IR reference product | 0.98 |
| Tmax (hr) CR product | 2.09 |

Example 6

The Pharmakokinetic parameters of Example 1, Example 4 and Example 5 were compared to each other. It was surprisingly found that even though the dissolution of the hydrocodone HCl controlled release tablets of example 1 were very similar to the dissolution of the controlled release oxycodone tablets of example 4 and the morphine sulfate controlled release tablets of example 5, the Cmax ratio of CR to IR for the hydrocodone formulation is 38%, whereas the oxycodone tablets and morphine tablets are over 50%. The comparative results are set forth in Table XIV below:

TABLE XIV

| Pharmacokinetic data | Hydrocodone Bitartrate | Oxycodone HCl | Morphine Sulphate |
|---|---|---|---|
| Cmax (ng/ml) IR reference product | 35.4 | 38.2 | 22.1 |
| Cmax (ng/ml) CR product | 13.4 | 21.7 | 12 |
| Cmax (CR)/Cmax (IR) | 38% | 57% | 54% |
| Tmax (hr) IR referencep product | 1.32 | 1.10 | 0.98 |
| Tmax (hr) CR product | 4.07 | 2.62 | 2.09 |

Example 7

A single dose, four treatment, open label, pharmacokinetic comparison of controlled release hydrocodone formulations of Example 1, Example 2, Example 3 and two immediate release hydrocodone bitartrate 7.5 mg/Acetaminophen 500 mg tablets (IR Example) in fasted normal volunteers was conducted. The plasma concentrations for these formulations are set forth in tables 15-18 below:

TABLE 15

Hydrocodone Plasma Concentration (ng/mL) after administration of one (1) Controlled-Release Hydrocodone Bitartrate 15 mg tablet-Formulation A

| Subject | −0.08 | 0.5 | 0.75 | 1 | 2 | 3 | 4 | 6 | 9 | 12 | 18 | 24 | 30 | 36 |
|---|---|---|---|---|---|---|---|---|---|---|---|---|---|---|
| 1 | 0.00 | 4.55 | 11.1 | 9.11 | 15.8 | 15.5 | 17.4 | 15.4 | 14.5 | 12.1 | 6.33 | 3.58 | 2.25 | 1.29 |
| 2 | 0.00 | 7.81 | 8.76 | 9.20 | 11.3 | 14.8 | 15.5 | 14.5 | 10.5 | 9.30 | 5.40 | 3.39 | 2.10 | 0.921 |
| 3 | 0.00 | 4.63 | 7.66 | 8.95 | 15.9 | 15.6 | 16.9 | 16.3 | 12.3 | 9.41 | 6.55 | 4.10 | 2.38 | 0.986 |
| 4 | 0.00 | 3.48 | 9.48 | 9.11 | 10.7 | 11.9 | 13.0 | 12.4 | 10.7 | 8.96 | 5.22 | 3.08 | 1.56 | 0.558 |
| 5 | 0.00 | 1.43 | 4.25 | 7.20 | 12.8 | 13.5 | 13.0 | 12.5 | 9.62 | 7.01 | 4.38 | 3.26 | 1.93 | 1.01 |
| 6 | 0.00 | 4.69 | 7.60 | 10.5 | 12.8 | 13.9 | 13.3 | 15.1 | 12.3 | 8.59 | 4.52 | 3.11 | 1.59 | 0.702 |
| 7 | 0.00 | 0.56 | 1.86 | 3.85 | 7.54 | 8.26 | 8.18 | 8.90 | 6.23 | 4.56 | 2.99 | 1.61 | 0.752 | 0.00 |
| 8 | 0.00 | 3.68 | 7.61 | 11.5 | 12.4 | 13.2 | 12.7 | 12.5 | 9.10 | 7.09 | 4.33 | 2.93 | 1.24 | 0.509 |
| 9 | 0.00 | 8.06 | 9.79 | 9.98 | 11.4 | 10.7 | 11.4 | 11.9 | 7.66 | 5.98 | 3.85 | 2.10 | 1.12 | 0.573 |
| 10 | 0.00 | 3.83 | 5.71 | 7.84 | 8.49 | 10.8 | 11.6 | 11.5 | 8.02 | 6.70 | 3.34 | 2.33 | 1.31 | 0.00 |
| 11 | 0.00 | 3.64 | 5.20 | 8.00 | 10.3 | 11.8 | 12.5 | 10.8 | 7.44 | 7.84 | 4.75 | 2.21 | 1.11 | 0.00 |
| 12 | 0.00 | 3.07 | 6.14 | 8.51 | 14.3 | 15.0 | 14.9 | 14.7 | 12.1 | 7.75 | 4.34 | 2.52 | 1.69 | 0.859 |
| 13 | 0.00 | 1.95 | 3.82 | 4.47 | 9.55 | 9.15 | 8.31 | 8.05 | 5.85 | 3.93 | 2.45 | 7.68 | 1.35 | 1.07 |
| 14 | 0.00 | 2.21 | 4.56 | 7.33 | 11.2 | 12.9 | 13.3 | 13.2 | 10.6 | 8.41 | 4.68 | 3.11 | 2.35 | 0.978 |
| MEAN | 0.00 | 3.83 | 6.68 | 8.25 | 11.7 | 12.6 | 13.0 | 12.7 | 9.78 | 7.69 | 4.51 | 3.22 | 1.62 | 0.675 |
| SD | 0.00 | 2.13 | 2.62 | 2.10 | 2.48 | 2.31 | 2.70 | 2.41 | 2.54 | 2.09 | 1.15 | 1.44 | 0.513 | 0.425 |
| % CV | 0.00 | 21.7 | 39.2 | 25.5 | 21.2 | 18.3 | 20.8 | 19.0 | 26.0 | 27.2 | 25.5 | 44.7 | 31.7 | 63.0 |

TABLE 16

Hydrocodone Plasma Concentration (ng/mL) after administration of one (1) Controlled-Release Hydrocodone Bitartrate 15 mg tablet-Formulation B

| Subject | −0.08 | 0.5 | 0.75 | 1 | 2 | 3 | 4 | 6 | 9 | 12 | 18 | 24 | 30 | 36 |
|---|---|---|---|---|---|---|---|---|---|---|---|---|---|---|
| 1 | 0.00 | 3.18 | 5.64 | 11.8 | 11.4 | 12.4 | 13.5 | 14.3 | 11.4 | 9.28 | 5.69 | 3.23 | 2.23 | 1.10 |
| 2 | 0.00 | 2.61 | 7.04 | 8.53 | 10.7 | 12.4 | 11.5 | 13.6 | 11.4 | 9.25 | 6.43 | 4.13 | 2.59 | 1.35 |

TABLE 16-continued

Hydrocodone Plasma Concentration (ng/mL) after administration of one (1) Controlled-Release Hydrocodone Bitartrate 15 mg tablet-Formulation B

| Subject | −0.08 | 0.5 | 0.75 | 1 | 2 | 3 | 4 | 6 | 9 | 12 | 18 | 24 | 30 | 36 |
|---|---|---|---|---|---|---|---|---|---|---|---|---|---|---|
| 3 | 0.00 | 5.49 | 7.57 | 9.67 | 13.5 | 15.6 | 15.7 | 14.4 | 12.6 | 9.41 | 7.83 | 5.19 | 3.45 | 1.77 |
| 4 | 0.00 | 2.71 | 5.67 | 6.35 | 8.88 | 11.3 | 13.7 | 12.0 | 8.72 | 8.18 | 5.58 | 4.33 | 2.63 | 1.26 |
| 5 | 0.00 | 3.98 | 6.59 | 7.38 | 10.6 | 11.8 | 11.6 | 9.42 | 6.75 | 4.81 | 5.28 | 3.67 | 2.43 | 1.25 |
| 6 | 0.00 | 0.711 | 2.85 | 7.98 | 12.9 | 13.6 | 13 | 13.8 | 10.1 | 8.04 | 5.17 | 3.71 | 2.33 | 0.940 |
| 7 | 0.00 | 1.82 | 3.03 | 3.97 | 7.22 | 8.04 | 8.05 | 7.87 | 5.97 | 3.77 | 2.53 | 2.12 | 1.94 | 1.19 |
| 8 | 0.00 | 2.47 | 3.99 | 6.03 | 10.9 | 13.2 | 13.8 | 12.6 | 9.49 | 7.60 | 6.11 | 4.74 | 2.38 | 0.856 |
| 9 | 0.00 | 5.02 | 10.4 | 8.48 | 9.06 | 9.90 | 9.88 | 7.96 | 4.78 | 3.99 | 3.77 | 3.42 | 1.53 | 0.805 |
| 10 | 0.00 | 3.20 | 8.17 | 10.7 | 9.08 | 10.7 | 11.8 | 11.2 | 9.08 | 6.20 | 3.38 | 2.75 | 1.84 | 0.672 |
| 11 | 0.00 | 4.20 | 6.86 | 6.36 | 9.97 | 11.3 | 11.3 | 10.2 | 7.79 | 5.08 | 4.38 | 2.67 | 1.53 | 0.815 |
| 12 | 0.00 | 4.73 | 7.71 | 9.48 | 11.9 | 15.1 | 16.5 | 15.5 | 13.2 | 8.89 | 4.58 | 3.60 | 2.67 | 2.12 |
| 13 | 0.00 | 1.56 | 2.87 | 3.89 | 6.31 | 7.43 | 7.87 | 7.64 | 7.01 | 5.34 | 3.57 | 2.12 | 1.35 | 1.41 |
| 14 | 0.00 | 0.663 | 2.20 | 3.86 | 8.74 | 14.7 | 15.0 | 15.3 | 13.6 | 10.7 | 6.84 | 4.47 | 2.39 | 1.59 |
| MEAN | 0 | 3.02 | 5.76 | 7.46 | 10.1 | 12 | 12.4 | 11.8 | 9.42 | 7.18 | 5.08 | 3.58 | 2.24 | 1.22 |
| SD | 0 | 1.53 | 2.45 | 2.53 | 2.03 | 2.45 | 2.61 | 2.81 | 2.77 | 2.27 | 1.48 | 0.943 | 0.556 | 0.408 |
| % CV | 0 | 50.7 | 42.5 | 33.9 | 20.1 | 20.4 | 21 | 23.8 | 29.4 | 31.6 | 29.1 | 26.3 | 24.8 | 33.4 |

TABLE 17

Hydrocodone Plasma Concentration (ng/mL) after administration of two (2) Immediate-Release Hydrocodone 7.5 mg/Acetaminophen 500 mg tablets-Formulation C

| Subject | −0.08 | 0.5 | 0.75 | 1 | 2 | 3 | 4 | 6 | 9 | 12 | 18 | 24 | 30 | 36 |
|---|---|---|---|---|---|---|---|---|---|---|---|---|---|---|
| 1 | 0.00 | 40.6 | 41.6 | 45.4 | 32.1 | 26.3 | 22.7 | 15.2 | 9.95 | 6.08 | 2.58 | 1.20 | 0.585 | 0.00 |
| 2 | 0.00 | 44.3 | 50.7 | 40.1 | 28.6 | 23.3 | 20.2 | 15.6 | 9.46 | 6.08 | 2.96 | 1.68 | 0.872 | 0.00 |
| 3 | 0.00 | 17.6 | 42.3 | 42.6 | 37.8 | 35.4 | 31.2 | 21.0 | 13.0 | 7.79 | 3.12 | 1.77 | 0.685 | 0.00 |
| 4 | 0.00 | 21.2 | 43.3 | 36.5 | 26.9 | 23.5 | 20.7 | 15.4 | 9.39 | 5.09 | 2.27 | 1.17 | 0.523 | 0.00 |
| 5 | 0.00 | 37.4 | 39.3 | 36.1 | 27.9 | 22.4 | 18.1 | 14.1 | 7.91 | 4.98 | 2.37 | 1.07 | 0.546 | 0.00 |
| 6 | 0.00 | 3.17 | 8.67 | 16.3 | 17.5 | 16.9 | 13.8 | 11.3 | 6.52 | 4.22 | 1.71 | 0.703 | 0.00 | 0.00 |
| 7 | 0.00 | 0.900 | 6.76 | 14.7 | 18.3 | 17.1 | 14.1 | 9.66 | 5.52 | 3.32 | 1.21 | 0.00 | 0.00 | 0.00 |
| 8 | 0.00 | 2.97 | 13.7 | 22.2 | 32.4 | 28.8 | 24.2 | 18.3 | 10.9 | 6.46 | 2.17 | 1.02 | 0.00 | 0.00 |
| 9 | 0.00 | 50.0 | 39.3 | 33.7 | 24.2 | 20.1 | 17.0 | 13.0 | 6.84 | 4.01 | 1.47 | 0.565 | 0.00 | 0.00 |
| 10 | 0.00 | 0.627 | 14.8 | 25.2 | 22.4 | 17.3 | 16.5 | 10.9 | 5.90 | 3.15 | 1.05 | 0.00 | 0.00 | 0.00 |
| 11 | 0.00 | 8.46 | 13.3 | 29.3 | 31.3 | 24.8 | 21.0 | 14.0 | 9.43 | 6.04 | 2.62 | 1.14 | 0.00 | 0.00 |
| 12 | 0.00 | 30.6 | 44.4 | 44.4 | 40.0 | 30.8 | 29.1 | 19.9 | 11.3 | 6.86 | 3.15 | 1.47 | 0.634 | 0.00 |
| 13 | 0.00 | 3.73 | 12.2 | 17.9 | 19.1 | 19.8 | 16.3 | 13.9 | 8.72 | 5.43 | 2.51 | 0.706 | 0.00 | 0.00 |
| 14 | 0.00 | 18.0 | 29.7 | 35.3 | 30.7 | 26.6 | 23.4 | 16.1 | 9.20 | 6.24 | 2.60 | 1.27 | 0.556 | 0.00 |
| MEAN | 0.00 | 20.0 | 28.6 | 31.4 | 27.8 | 23.8 | 20.6 | 14.9 | 8.86 | 5.41 | 2.27 | 0.983 | 0.314 | 0.00 |
| SD | 0.00 | 17.7 | 16.0 | 10.6 | 6.93 | 5.48 | 5.21 | 3.26 | 2.15 | 1.36 | 0.676 | 0.541 | 0.336 | 0.00 |
| % CV | 0.00 | 88.5 | 55.9 | 33.8 | 24.9 | 23.0 | 25.3 | 21.9 | 24.3 | 25.1 | 29.8 | 55.0 | 107 | 0.00 |

TABLE 18

Hydrocodone Plasma Concentration (ng/mL) after administration of one (1) Controlled-Release Hydrocodone Bitartrate 15 mg capsule-Formulation D

| Subject | −0.08 | 0.5 | 0.75 | 1 | 2 | 3 | 4 | 6 | 9 | 12 | 18 | 24 | 30 | 36 |
|---|---|---|---|---|---|---|---|---|---|---|---|---|---|---|
| 1 | 0.00 | 1.76 | 4.07 | 5.17 | 8.33 | 9.72 | 11.1 | 14.0 | 13.6 | 11.7 | 8.78 | 6.14 | 3.91 | 1.97 |
| 2 | 0.00 | 2.76 | 4.83 | 5.13 | 6.17 | 10.4 | 10.6 | 13.5 | 11.8 | 10.1 | 6.57 | 3.71 | 2.57 | 1.34 |
| 3 | 0.00 | 2.91 | 4.25 | 6.01 | 10.1 | 12.3 | 12.0 | 14.8 | 13.5 | 11.4 | 7.40 | 4.16 | 2.65 | 1.46 |
| 4 | 0.00 | 1.69 | 5.93 | 6.26 | 8.29 | 8.37 | 8.06 | 10.5 | 8.91 | 8.70 | 4.58 | 2.61 | 1.63 | 0.536 |
| 5 | 0.00 | 0.616 | 2.74 | 4.47 | 8.58 | 9.16 | 8.60 | 10.1 | 8.66 | 6.64 | 4.72 | 2.57 | 2.05 | 0.986 |
| 6 | 0.00 | 0.663 | 2.40 | 4.87 | 7.50 | 10.1 | 11.7 | 13.0 | 11.5 | 8.30 | 5.38 | 3.88 | 2.39 | 1.25 |
| 7 | 0.00 | 0.00 | 1.55 | 2.32 | 4.61 | 6.38 | 7.22 | 7.41 | 6.75 | 4.82 | 3.10 | 1.72 | 0.984 | 0.578 |
| 8 | 0.00 | 1.26 | 3.03 | 5.15 | 7.26 | 8.80 | 8.81 | 9.34 | 9.07 | 9.28 | 6.81 | 3.31 | 1.93 | 1.25 |
| 9 | 0.00 | 3.36 | 3.63 | 6.38 | 8.31 | 8.04 | 8.20 | 9.55 | 8.28 | 6.49 | 3.72 | 2.25 | 1.92 | 0.901 |
| 10 | 0.00 | 0.692 | 2.91 | 2.95 | 5.11 | 6.09 | 7.37 | 7.11 | 6.33 | 5.67 | 3.76 | 2.76 | 1.43 | 0.573 |
| 11 | 0.00 | 1.11 | 2.87 | 3.28 | 6.82 | 9.69 | 10.3 | 12.0 | 12.2 | 8.81 | 5.76 | 3.25 | 2.10 | 1.08 |
| 12 | 0.00 | 2.25 | 3.31 | 4.72 | 8.03 | 11.4 | 11.2 | 12.1 | 11.0 | 9.75 | 5.64 | 3.51 | 2.71 | 1.34 |

TABLE 18-continued

Hydrocodone Plasma Concentration (ng/mL) after administration of one (1) Controlled-Release Hydrocodone Bitartrate 15 mg capsule-Formulation D

| | Time (hours) | | | | | | | | | | | | | |
|---|---|---|---|---|---|---|---|---|---|---|---|---|---|---|
| Subject | −0.08 | 0.5 | 0.75 | 1 | 2 | 3 | 4 | 6 | 9 | 12 | 18 | 24 | 30 | 36 |
| 13 | 0.00 | 0.00 | 1.29 | 2.71 | 5.51 | 6.67 | 8.92 | 8.44 | 7.13 | 7.01 | 3.99 | 2.41 | 1.04 | 0.858 |
| 14 | 0.00 | 1.02 | 2.94 | 4.53 | 8.82 | 10.5 | 11.7 | 14.1 | 13.0 | 10.2 | 6.37 | 3.56 | 1.93 | 1.61 |
| MEAN | 0.00 | 1.44 | 3.27 | 4.57 | 7.39 | 9.12 | 9.70 | 11.1 | 10.1 | 8.49 | 5.47 | 3.27 | 2.09 | 1.12 |
| SD | 0.00 | 1.06 | 1.23 | 1.31 | 1.57 | 1.86 | 1.71 | 2.57 | 2.65 | 2.11 | 1.61 | 1.08 | 0.754 | 0.419 |
| % CV | 0.00 | 73.6 | 37.6 | 28.7 | 21.2 | 20.4 | 17.6 | 23.2 | 25.2 | 24.9 | 29.4 | 33.0 | 36.1 | 37.4 |

TABLE 19

| Parameter | Mean[a] | | % Ratio[b,c] | 90% CI[b] | |
|---|---|---|---|---|---|
| | Ex. 1 Fasted | IR Ex. Fasted | Ex. 1/IR Ex. Fasted | Lower | Upper |
| AUC(0, last) (ng · hr/mL) | 200.95 | 216.35 | 93.36 | 86.96 | 100.23 |
| Cmax (ng/mL) | 13.16 | 33.37 | 39.48 | 35.26 | 44.20 |
| Tmax (hr) | 4.07 | 1.32 | 208.11 | 257.17 | 357.80 |
| W50 (hr) | 13.41 | 4.67 | 287.38 | 265.91 | 314.15 |
| T½(abs) (hr) | 1.64 | 0.69 | 237.65 | 197.73 | 284.44 |
| T½(elim) (hr) | 6.44 | 3.09 | 208.78 | 184.43 | 234.20 |
| | Ex. 2 Fasted | IR Ex. Fasted | Ex. 2/IR Ex. Fasted | Lower | Upper |
| AUC(0, last) (ng · hr/mL) | 201.57 | 216.35 | 93.21 | 86.82 | 100.07 |
| Cmax (ng/mL) | 12.42 | 33.37 | 37.36 | 33.37 | 41.83 |
| Tmax (hr) | 4.20 | 1.32 | 317.57 | 262.19 | 362.83 |
| W50 (hr) | 13.08 | 4.67 | 280.31 | 257.03 | 305.26 |
| T½(abs) (hr) | 1.57 | 0.69 | 227.91 | 183.84 | 270.55 |
| T½(elim) (hr) | 7.86 | 3.09 | 254.85 | 231.54 | 281.31 |
| | Ex. 3 Fasted | IR. Ex. Fasted | Ex. 3/IR Ex. Fasted | Lower | Upper |
| AUC(0, last) (ng · hr/mL) | 194.40 | 216.35 | 90.28 | 84.09 | 96.92 |
| Cmax (ng/mL) | 10.93 | 33.37 | 32.69 | 29.20 | 36.60 |
| Tmax (hr) | 5.93 | 1.32 | 448.65 | 398.87 | 499.51 |
| W50 (hr) | 16.30 | 4.67 | 349.21 | 328.68 | 376.92 |
| T½(abs) (hr) | 2.98 | 0.69 | 431.26 | 395.95 | 482.67 |
| T½(elim) (hr) | 6.96 | 3.09 | 225.61 | 200.49 | 250.26 |

[a]Geometric means for AUC(0, last) and Cmax and arithmetic means for Tmax, W50, T½(abs), and T½(elim).
[b]Ratio and 90% Cl are based on least square means.
[c]Ratio (%): (Test mean/Reference mean) × 100, based on least square means Example 8

Hydrocodone sustained release tablets were produced with the formula set forth in Table XX below:

TABLE XX

| Ingredient | mg/tab | kg/batch |
|---|---|---|
| Hydrocodone bitartrate | 15 | 15.0 |
| Dibasic calcium phosphate | 31 | 31.0 |
| Glyceryl behenate | 10 | 10.0 |
| Stearyl alcohol | 22 | 22.0 |
| Microcrystalline cellulose | 31 | 31.0 |
| Magnesium stearate | 1.0 | 1.0 |
| Opadry Purple YS-1-10371-A | 5.0 | 5.0 |
| Purified water | N/A[1] | 28.33[1] |
| | 115.0 mg | 115.0 kg |

[1]Evaporates during processing and is not part of finished product.

According to the following procedure:

1. Milling: Pass stearyl alcohol flakes through a mill.
2. Blending: Mix The Hydrocodone bitartrate, Dibasic calcium phosphate, Glyceryl behenate, Stearyl alcohol and Microcrystalline cellulose with a suitable blender
3. Extrusion: Continuously feed the blended material into a twin screw extruder at an elevated temperature to soften and form an extrudate.
4. Cooling: Allow the extrudate to cool on a Conveyor.
5. Milling: Pass the cooled extrudate through a mill to obtain a suitable particle size granulation
6. Blending: Blend the milled extrudate with the magnesium stearate.
7. Compression: Compress the resultant granulation using a tablet press.
8. Coating: Prepare a film coating solution by dispersing the Opadry in Purified Water and applying it to the tablet cores.

The tablets were then tested for dissolution using the following procedure:

1. Apparatus: USP Type I (basket), 100 rpm.
2. Medium: 700 ml SGF (without enzymes) for first 55 minutes, thereafter made 900 ml with phosphate buffer to pH 7.5.
3. Sampling time: 1, 2, 4, 8, and 12 hours.
4. Analytical: High Performance Liquid Chromatography.

The dissolution parameters are set forth in Table XXI below:

TABLE XXI

| Time (hrs) | % Dissolved |
|---|---|
| 1 | 22 |
| 2 | 37 |
| 4 | 58 |
| 8 | 84 |
| 12 | 99 |

Example 9

A 3 way crossover, pharmakokinetic comparison study of a single dose of 15 mg Hydrocodone Controlled Release Tablets (Example 8) in Fed and Fasted and of 15 mg Hydrocodone Immediate Release Tablets) was given over two Q6H doses in fasted normal volunteers.

The Cmax and Tmax were then obtained for Example 8 and an immediate release reference standard in a bioavailablity study, as set forth in Table XXII and XXIII below:

TABLE XXII

| Pharmacokinetic data (Fasted State) | Hydrocodone Bitartrate |
|---|---|
| Cmax (ng/ml) IR reference product (Dose adjusted) | 43.16 |
| Cmax (ng/ml) CR product | 17.87 |
| Cmax (CR)/Cmax (IR) | 41% |
| Tmax (hr) IR reference product | 6.42 |
| Tmax (hr) CR product | 4.04 |

TABLE XXXIII

| Pharmacokinetic data | Hydrocodone Bitartrate CR 15 mg Tablets (Fasted) | Hydrocodone Bitartrate CR 15 mg Tablets (Fed) | Hydrocodone Bitartrate IR 2 × 7.5 mg Tablets (Fasted) |
|---|---|---|---|
| Cmax (ng/ml) | 17.87 | 19.23 | 21.58 |
| $C_{12\ hour}$ | 11.06 | 12.84 | |
| $C_{12\ hour}$/Cmax | 62% | 67% | |
| Tmax(hr) | 4.04 | 4.81 | 6.42 |
| AUC | 267.43 | 277.58 | 229.33 |

We claim:

1. A twice-a-day solid controlled-release oral dosage form, the dosage form comprising
a controlled-release matrix comprising
(i) hydrocodone bitartrate in an amount from about 0.5 mg to about 1250 mg of hydrocodone and
(ii) an effective amount of a controlled release material to render the dosage form suitable for twice-a-day administration, wherein the controlled release material is selected from the group consisting of
a mixture of (a) a copolymer of acrylic and methacrylic ester with a molar ratio of ammonium groups to neutral (meth)acrylic esters of 1:20, (b) a copolymer of acrylic and methacrylic ester with a molar ratio of ammonium groups to neutral (meth)acrylic esters of 1:40, and (c) stearyl alcohol;
a mixture of (a) a copolymer of acrylic and methacrylic ester with a molar ratio of ammonium groups to neutral (meth)acrylic esters of 1:40, (b) triacetin and (c) stearyl alcohol; and
a mixture of (a) microcrystalline cellulose, (b) stearyl alcohol, and (c) glyceryl behenate,
said dosage form providing an in-vitro release of from 18% to about 42.5% by weight of the hydrocodone from the dosage form at one hour, when measured by the USP Basket Method at 100 rpm in 700 ml of Simulated Gastric Fluid (SGF) for 55 minutes at 37° C. and thereafter 900 ml of Simulated Intestinal Fluid (SIF) without enzyme,
from about 25 to about 65% by weight of the hydrocodone after 2 hours, from about 45 to about 85% by weight of the hydrocodone after 4 hours, and greater than about 60% by weight of the hydrocodone after 8 hours, when measured by the USP Basket method at 100 rpm in 900 ml aqueous buffer at a pH of 1.2 at 37° C.; and
after a first administration to a human patient,
a therapeutic effect for about 12 hours,
a flat plasma concentration profile of hydrocodone such that a plasma concentration of hydrocodone after attaining a maximum plasma concentration during the dosing interval stays within from about 60 to about 100% of the maximum plasma concentration for the remainder of the dosing interval,
a plasma concentration of hydrocodone of at least 8 ng/ml at from about 2 to about 8 hours after administration and of at least 6 ng/ml at about 12 hours after administration, based on oral administration of the dosage form containing 15 mg hydrocodone bitartrate,
a rate of absorption during the time period from $T_{max}$ to about 12 hours after oral administration of the dosage form which is from about 60% to about 100% of the rate of elimination during the same time period, and
a $C_{max}$ of hydrocodone which is less than 50% of the $C_{max}$ of an equivalent dose of an immediate release hydrocodone reference formulation.

2. The dosage form of claim 1, wherein the dosage form provides
the flat plasma concentration profile of hydrocodone such that the plasma concentration of hydrocodone after attaining the maximum plasma concentration during the dosing interval stays within about 60% of the maximum plasma concentration for the remainder of the dosing interval.

3. The dosage form of claim 1, wherein the amount is from about 5 mg to about 60 mg.

4. The dosage form of claim 1, wherein the amount is 15 mg.

5. The twice-a-day solid controlled-release oral dosage form of claim 1, the dosage form providing
the flat plasma concentration profile of hydrocodone such that the plasma concentration of hydrocodone after attaining the maximum plasma concentration during the dosing interval stays within about 65% of the maximum plasma concentration for the remainder of the dosing interval.

6. The dosage form of claim 1, wherein the rate of absorption during the time period from $T_{max}$ to about 12 hours after oral administration of the dosage form is from about 60% of the rate of elimination during the same time period.

7. The twice-a-day solid controlled-release oral dosage form of claim 1, the dosage form providing
the flat plasma concentration profile of hydrocodone such that the plasma concentration of hydrocodone after attaining the maximum plasma concentration during the dosing interval stays within about 75% of the maximum plasma concentration for the remainder of the dosing interval.

8. The dosage form of claim 1 which provides the rate of absorption during the time period from $T_{max}$ to about 12 hours after oral administration of the dosage form is about 85% of the rate of elimination during the same time period.

9. The dosage form of claim 1, wherein the controlled release material is the mixture of (a) a copolymer of acrylic and methacrylic ester with a molar ratio of ammonium groups to neutral (meth)acrylic esters of 1:20, (b) a copolymer of acrylic and methacrylic ester with a molar ratio of ammonium groups to neutral (meth)acrylic esters of 1:40, and (c) stearyl alcohol.

10. The dosage form of claim 1, wherein the dosage form provides the flat plasma concentration profile of hydrocodone such that the plasma concentration of hydrocodone after attaining the maximum plasma concentration during the dosing interval stays within about 80% of the maximum plasma concentration for the remainder of the dosing interval.

11. The dosage form of claim 10, wherein said matrix is in a multiparticulate form.

12. The dosage form of claim 11, wherein said multiparticulate form is disposed in a pharmaceutically acceptable capsule.

13. The dosage form of claim 10, which provides the $T_{max}$ of hydrocodone in said patient at from about 2 to about 8 hours after oral administration of the dosage form.

14. The dosage form of claim 10, which provides the $T_{max}$ of hydrocodone in said patient at from about 3 to about 7 hours after oral administration of the dosage form.

15. The dosage form of claim 10, which provides the $T_{max}$ of hydrocodone in said patient at from about 4 to about 6 hours after oral administration of the dosage form.

16. The dosage form of claim 10, which provides a plasma concentration of hydrocodone of at least 8 ng/ml at from about 3 to about 7 hours after administration.

17. The dosage form of claim 10 which provides a time to 90% mean $C_{max}$ of hydrocodone from of about 1.5 to about 2.5 hours.

18. The dosage form of claim 10 which provides a time to 90% mean $C_{max}$ of hydrocodone from about 1.8 to about 2.2 hours.

19. The dosage form of claim 10 which after attaining the maximum plasma concentration maintains a plasma concentration within 80% of the maximum plasma concentration for about 1 to about 9 hours.

20. The dosage form of claim 10 which after attaining the maximum plasma concentration maintains a plasma concentration within 85% of the maximum plasma concentration for about 4 to about 8 hours.

21. The dosage form of claim 10 which after attaining the maximum plasma concentration maintains a plasma concentration within 90% of the maximum plasma concentration for about 1 to about 6.5 hours.

22. The dosage form of claim 10 which after attaining the maximum plasma concentration maintains a plasma concentration within 90% of the maximum plasma concentration for about 2 to about 5 hours.

23. The dosage form of claim 10, which provides a mean in-vivo absorption rate from administration to $T_{max}$ of from about 1.5 mg/hour to about 5 mg/hour and a mean rate of absorption from $T_{max}$ to the end of the dosing interval which is less than about 0.5 mg/hour, based on oral administration of the dosage form of claim 1 containing 15 mg hydrocodone bitartrate.

24. The dosage form of claim 23 which provides the mean in-vivo absorption rate from administration to $T_{max}$ of from about 2 mg/hour to about 4 mg/hour.

25. The dosage form of claim 23 which provides the mean in-vivo absorption rate $T_{max}$ to the end of the dosing interval of from about 0.08 mg/hour to about 0.4 mg/hour.

26. The dosage form of any one of claim 1, 2, 4, 5, 7, 15, or 23, wherein a portion of the hydrocodone is in immediate release form and is coated over the controlled release matrix.

27. The dosage form of claim 26 which after attaining the maximum plasma concentration maintains a plasma concentration within 90% of the maximum plasma concentration for about 6.5 hours.

28. The dosage form of any one of 1, 2, 4, 5, 7, 15, or 23, wherein the controlled release material is the mixture of (i) the copolymer of acrylic and methacrylic ester with a molar ratio of ammonium groups to neutral (meth)acrylic esters of 1:40, (ii) triacetin and (iii) stearyl alcohol.

29. The dosage form of any one of claim 1, 2, 4, 5, 7, 15, or 23, wherein the controlled release material is the mixture of (i) microcrystalline cellulose, (ii) stearyl alcohol, and (iii) glyceryl behenate.

* * * * *